(12) United States Patent
DeMuth et al.

(10) Patent No.: US 9,610,252 B2
(45) Date of Patent: Apr. 4, 2017

(54) MULTILAYER COMPOSITIONS, COATED DEVICES AND USE THEREOF

(71) Applicant: Massachusetts Institute of Technology, Cambridge, MA (US)

(72) Inventors: Peter DeMuth, Cambridge, MA (US); Younjin Min, Cambridge, MA (US); Darrell Irvine, Arlington, MA (US); Paula T. Hammond, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/435,057

(22) PCT Filed: Oct. 11, 2013

(86) PCT No.: PCT/US2013/064530
§ 371 (c)(1),
(2) Date: Apr. 10, 2015

(87) PCT Pub. No.: WO2014/059269
PCT Pub. Date: Apr. 17, 2014

(65) Prior Publication Data
US 2015/0250739 A1 Sep. 10, 2015

Related U.S. Application Data

(60) Provisional application No. 61/713,457, filed on Oct. 12, 2012.

(51) Int. Cl.
| | | |
|---|---|---|
| A61K 9/50 | (2006.01) |
| A61K 9/70 | (2006.01) |
| B05D 1/36 | (2006.01) |
| A61K 9/00 | (2006.01) |
| C12N 15/89 | (2006.01) |
| A61K 39/21 | (2006.01) |
| A61K 47/32 | (2006.01) |
| A61K 47/34 | (2017.01) |

(Continued)

(52) U.S. Cl.
CPC .......... *A61K 9/7007* (2013.01); *A61K 9/0021* (2013.01); *A61K 9/5084* (2013.01); *A61K 39/21* (2013.01); *A61K 47/32* (2013.01); *A61K 47/34* (2013.01); *B05D 1/36* (2013.01); *C12N 7/00* (2013.01); *C12N 15/89* (2013.01); *A61K 2039/53* (2013.01); *A61K 2039/55511* (2013.01); *C12N 2740/16234* (2013.01)

(58) Field of Classification Search
CPC ............................. A61K 9/5084; B05D 1/36
See application file for complete search history.

(56) References Cited

U.S. PATENT DOCUMENTS

2009/0088679 A1* 4/2009 Wood ................... A61K 9/0009
604/20
2012/0027837 A1* 2/2012 DeMuth ............... A61K 9/0021
424/443

* cited by examiner

*Primary Examiner* — Carlos Azpuru
(74) *Attorney, Agent, or Firm* — Foley Hoag LLP

(57) ABSTRACT

The present invention provides, among other things, multilayer film coating compositions, coated substrates and methods thereof. In some embodiments, a structure, comprising a substrate and a multilayer film on the substrate, wherein the multilayer film comprises a release layer and one or more layer-by-layer films. In some embodiments, a structure comprising a microneedle substrate and a multilayer film coated on at least portion of the microneedle substrate, wherein the multilayer film comprises an agent for delivery.

29 Claims, 29 Drawing Sheets

(51) Int. Cl.
*C12N 7/00* (2006.01)
*A61K 39/00* (2006.01)

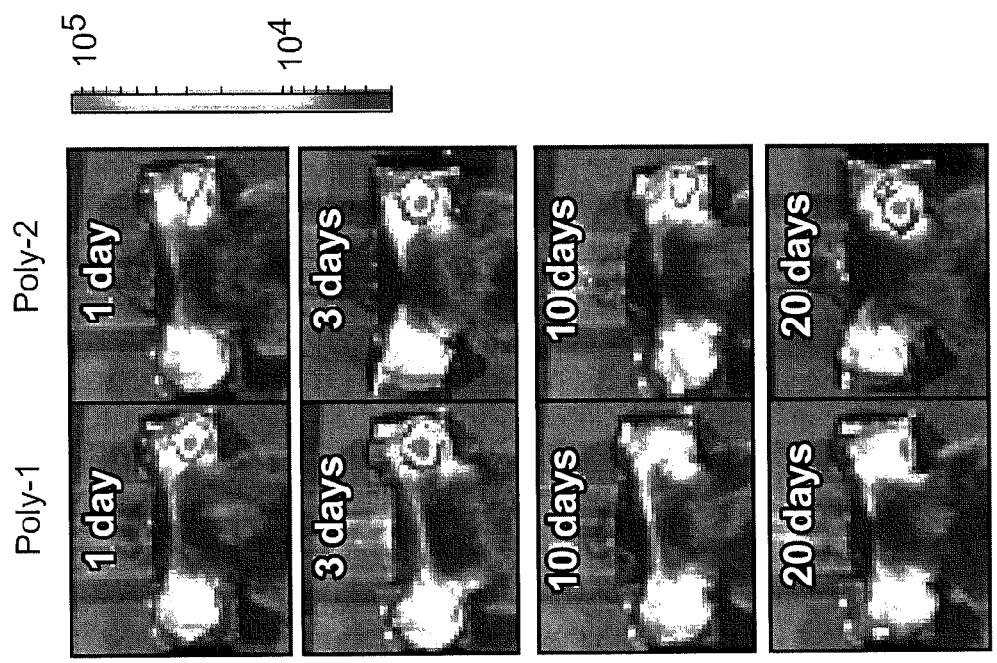
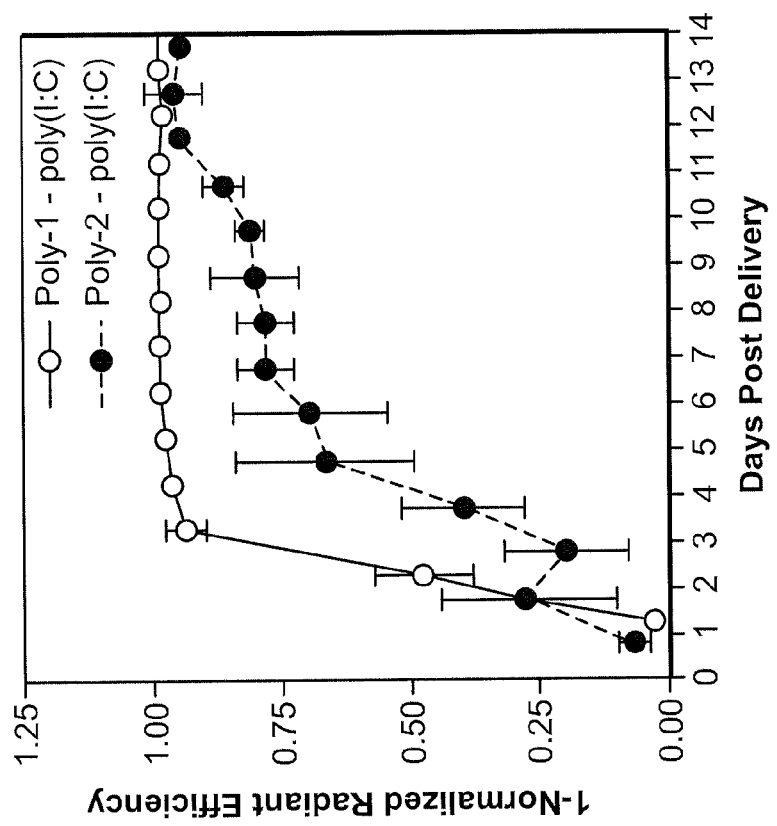
FIG. 4D
FIG. 4C

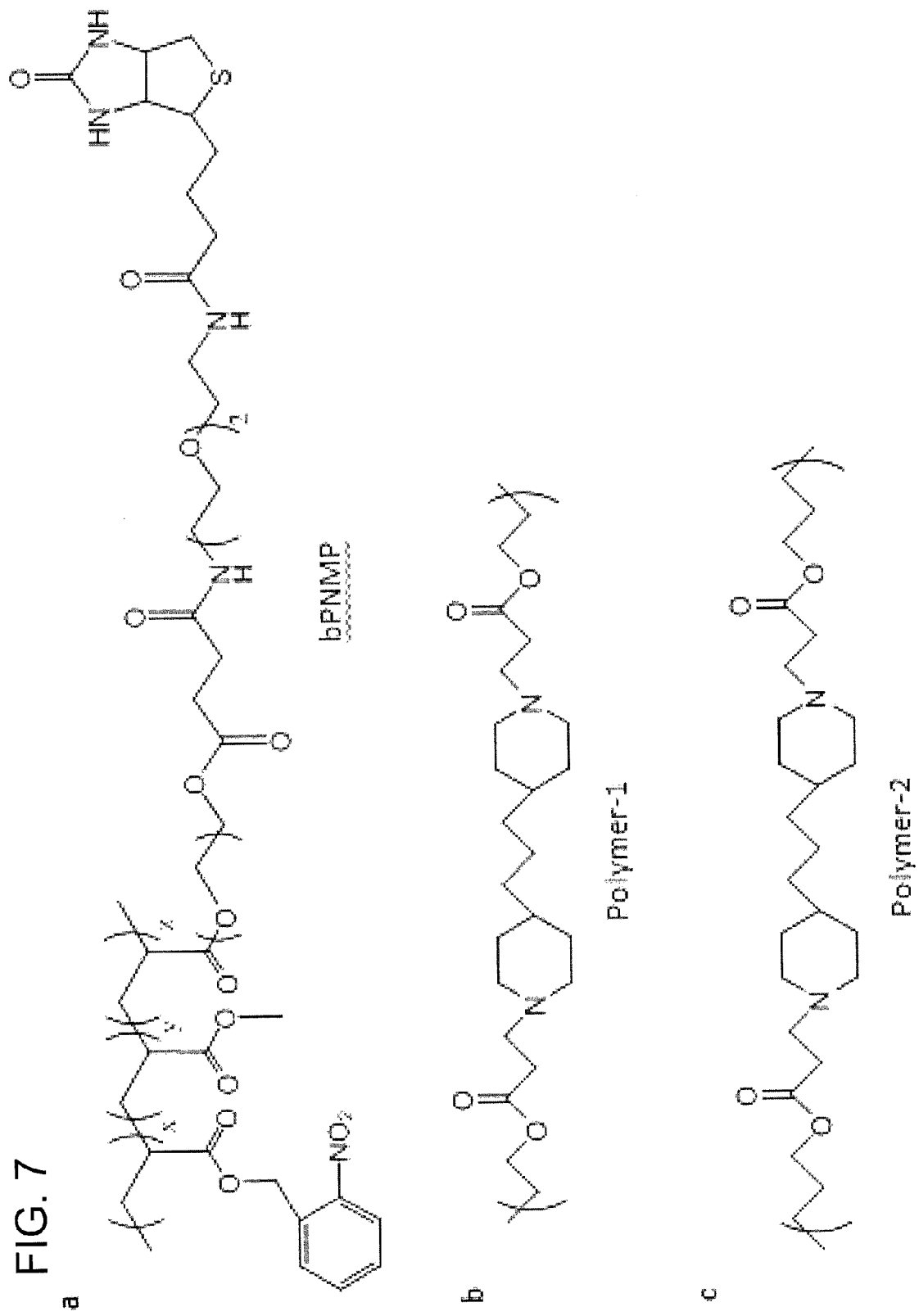

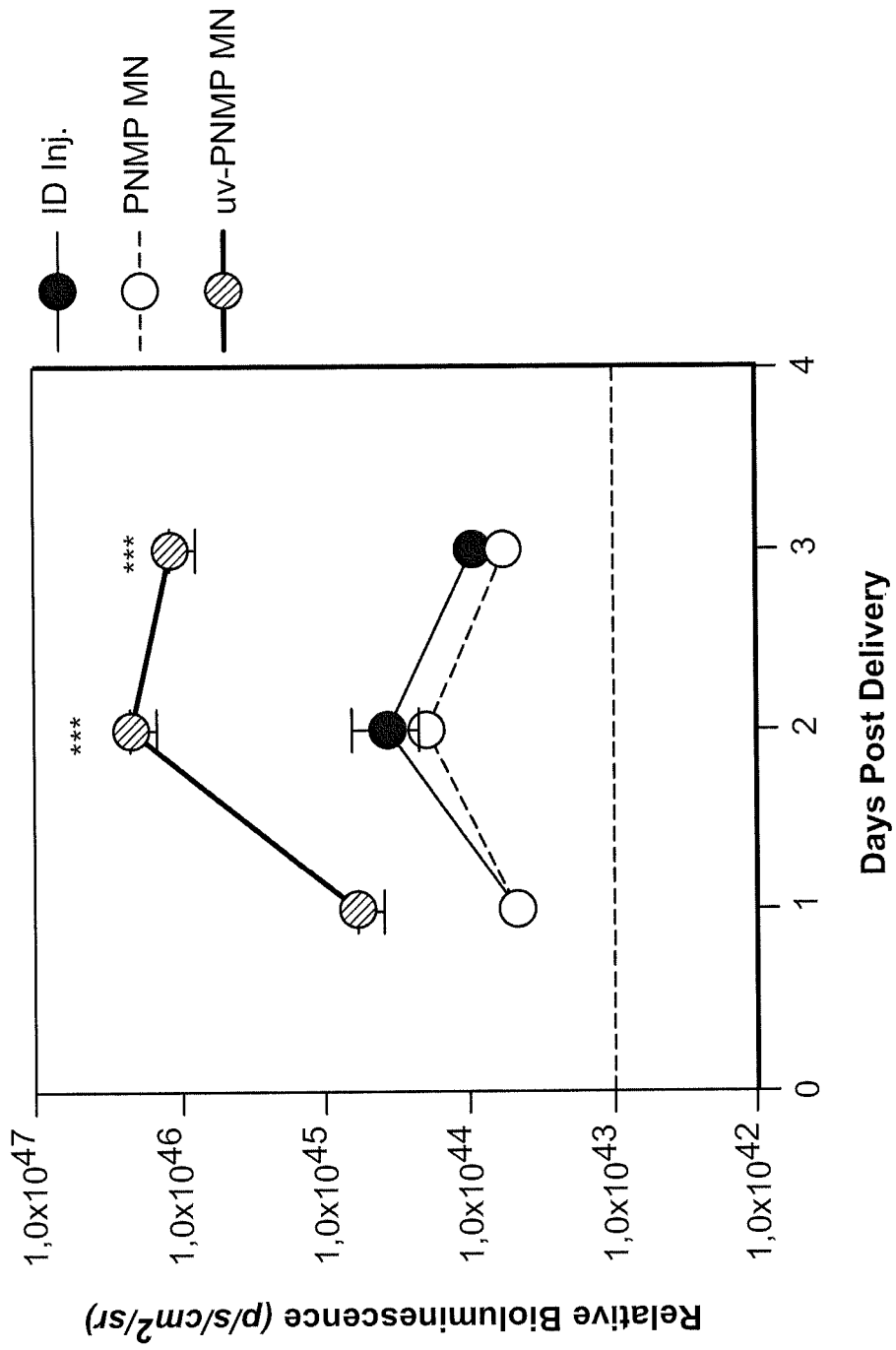

MULTILAYER COMPOSITIONS, COATED DEVICES AND USE THEREOF

This application is the U.S. National Stage of International Application No. PCT/US2013/064530, filed Oct. 11, 2013, which designates the U.S., published in English, and claims the benefit of U.S. Provisional Application No. 61/713,457, filed Oct. 12, 2012. The entire teachings of the above applications are incorporated herein by reference.

BACKGROUND

Layer-by-Layer (LBL) assembly of multilayer film coatings is driven by the alternating deposition of materials (e.g., polymers with complementary electrostatic functionalities). The LBL assembly process produces nanometer to micron scale thin film coatings. A major benefit of LBL assembly is the potential to achieve controlled and sequential delivery of agents by tuning the deposition of these agents at specific layers within the film.

There is a particular interest in achieving delivery of vaccines and/or therapeutic agents by taking advantage of LBL films. Delivery through the skin (i.e., transcutaneous delivery) is a focus of much research. Thus, there is a need in the art for versatile platform for delivery, particularly transcutaneous delivery of drugs and other agents that is effective, generally applicable, safe, pain-free, and/or cost effective.

SUMMARY

The present invention provides, among other things, a release layer. Various structures comprising substrates coated with such a release layer alone or in combination with other films/layers (e.g., LBL films) are provided. In some embodiments, a release layer is or comprises a polymer, which is stable during deposition/assembly onto a substrate and can be converted and become unstable when exposed in a liquid medium under certain conditions for releasing.

In one aspect, the invention provides certain multilayer films comprising LBL films and at least one release layer, for example as a coating composition on a substrate. In some embodiments, such multilayer films, for example, at least a portion of LBL films, are associated with one or more agents for delivery. Multilayer film compositions can be particularly useful for DNA delivery in certain embodiments.

In one aspect, the invention provides a structure comprising a substrate arranged and constructed for contact with a biological tissue; such a substrate being coated with a multilayer film coating composition. In some embodiments, such a substrate is or comprises a microneedle or a microneedle array.

Among other things, the present invention demonstrates and achieves various improvements in microneedle devices, and particularly in delivery of nucleic acids together with other agents such as transfection and/or immunological agents from the devices.

It is recognized in the present invention that a underlying release layer enables a rapid release of LBL films or other outer layers/films from a coated substrate. For example, coated microneedles can be used to rapidly implant drug delivery films by brief application to a tissue (e.g., skin), which allows the kinetics of the agent for delivery from the films in the tissue to be tailored separately from the time required for microneedles to be kept in contact with the tissue.

The present invention also encompasses the recognition that, in many cases, combining the flexible and highly tunable nature of provided multilayer films with microneedle devices provides a versatile platform for delivery of a variety of agents.

The present invention also provides methods of making and using provided structures and/or multilayer films.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

DEFINITIONS

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated moieties are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component polymers. In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages "Hydrolytically degradable": As used herein, "hydrolytically degradable" materials are those that degrade by hydrolytic cleavage. In some embodiments, hydrolytically degradable materials degrade in water. In some embodiments, hydrolytically degradable materials degrade in water in the absence of any other agents or materials. In some embodiments, hydrolytically degradable materials degrade completely by hydrolytic cleavage, e.g., in water. By contrast, the term "non-hydrolytically degradable" typically refers to materials that do not fully degrade by hydrolytic cleavage and/or in the presence of water (e.g., in the sole presence of water).

"Nucleic acid": The term "nucleic acid" as used herein, refers to a polymer of nucleotides. In some embodiments, nucleic acids are or contain deoxyribonucleic acids (DNA); in some embodiments, nucleic acids are or contain ribonucleic acids (RNA). In some embodiments, nucleic acids include naturally-occurring nucleotides (e.g., adenosine, thymidine, guanosine, cytidine, uridine, deoxyadenosine, deoxythymidine, deoxyguanosine, and deoxycytidine). Alternatively or additionally, in some embodiments, nucleic acids include non-naturally-occurring nucleotides including, but not limited to, nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups. In some embodiments, nucleic acids include phosphodiester backbone linkages; alternatively or additionally, in some embodiments, nucleic acids include one or more non-phosphodiester backbone linkages such as, for example, phosphorothioates and 5'-N-phosphoramidite linkages. In some embodiments, a nucleic acid is an oligonucleotide in that it is relatively short (e.g., less that about 5000, 4000, 3000, 2000, 1000, 900, 800, 700, 600, 500, 450, 400, 350, 300, 250, 200, 150, 100, 90, 80, 70, 60, 50, 45, 40, 35, 30, 25, 20, 15, 10 or fewer nucleotides in length.

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

"Polyelectrolyte": The term "polyelectrolyte", as used herein, refers to a polymer which under some set of conditions (e.g., physiological conditions) has a net positive or negative charge. Polyelectrolytes includes polycations and polyanions. Polycations have a net positive charge and polyanions have a net negative charge. The net charge of a given polyelectrolyte may depend on the surrounding chemical conditions, e.g., on the pH.

"Polypeptide": The term "polypeptide" as used herein, refers to a string of at least three amino acids linked together by peptide bonds. Polypeptides such as proteins may contain only natural amino acids, although non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in a protein may be modified, for example, by the addition of a chemical entity such as a carbohydrate group, a phosphate group, a farnesyl group, an isofarnesyl group, a fatty acid group, a linker for conjugation, functionalization, or other modification, etc.

"Polysaccharide": The term "polysaccharide" refers to a polymer of sugars. Typically, a polysaccharide comprises at least three sugars. In some embodiments, a polypeptide comprises natural sugars (e.g., glucose, fructose, galactose, mannose, arabinose, ribose, and xylose); alternatively or additionally, in some embodiments, a polypeptide comprises one or more non-natural amino acids (e.g, modified sugars such as 2'-fluororibose, 2'-deoxyribose, and hexose).

"Small molecule": As used herein, the term "small molecule" is used to refer to molecules, whether naturally-occurring or artificially created (e.g., via chemical synthesis), that have a relatively low molecular weight. Typically, small molecules are monomeric and have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered acceptable for use in accordance with the present application.

"Substantially": As used herein, the term "substantially", and grammatic equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Treating": As used herein, the term refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

**, $p<0.005$, analyzed by two-way analysis of variance

FIG. 6 illustrates exemplary microneedle fabrication. a, PDMS is laser ablated to form micron-scale cavities. b, PLLA is added to the surface of the PDMS mold. c, PLLA is melted under vacuum and then cooled before d, removal of PLLA microneedle arrays. e, SEM and f, optical micrograph of PLLA microneedle arrays produced through PDMS melt-casting (scale bar—500 µm.

FIG. 7 shows chemical structure of polymers. a, Structure of biotinylated-PNMP (bPNMP, MW~17,000 Da) in which a pendant biotin is conjugated to the free hydroxyl terminus of the PEG-methacrylate monomer unit. b, Chemical structure of poly-1 (MW~15,000 Da) and c, poly-2 (MW~21,000 Da) used in this study.

FIG. 8 illustrates that multi-layer deposition is controllable and modular. a, Film growth for $(poly-1/poly(I:C))_n$ and $(poly-2/poly(I:C))_n$ multi-layers assembled following uv-PNMP and $(PS/SPS)_{20}$ deposition on silicon. b, Representative confocal images of an SAv488-bPNMP-(PS/SPS)

$_{20}$-(poly-1/TMR-poly(I:C))$_{35}$ coated microneedle (left—transverse sections, right—lateral sections, 100 µm interval, scale—200 µm, blue—Sav488-bPNMP, red—TMR-poly(I:C)). c, Quantification of encapsulated TMR-poly(I:C) dosage through confocal image analysis (left axis, n=15) and film elution (right axis, n=3). d, Film growth for (poly-1/pLUC) and (poly-1/poly(I:C)) multi-layers assembled following uv-PNMP and (PS/SPS)$_{20}$ deposition on silicon.

Figure 9A:
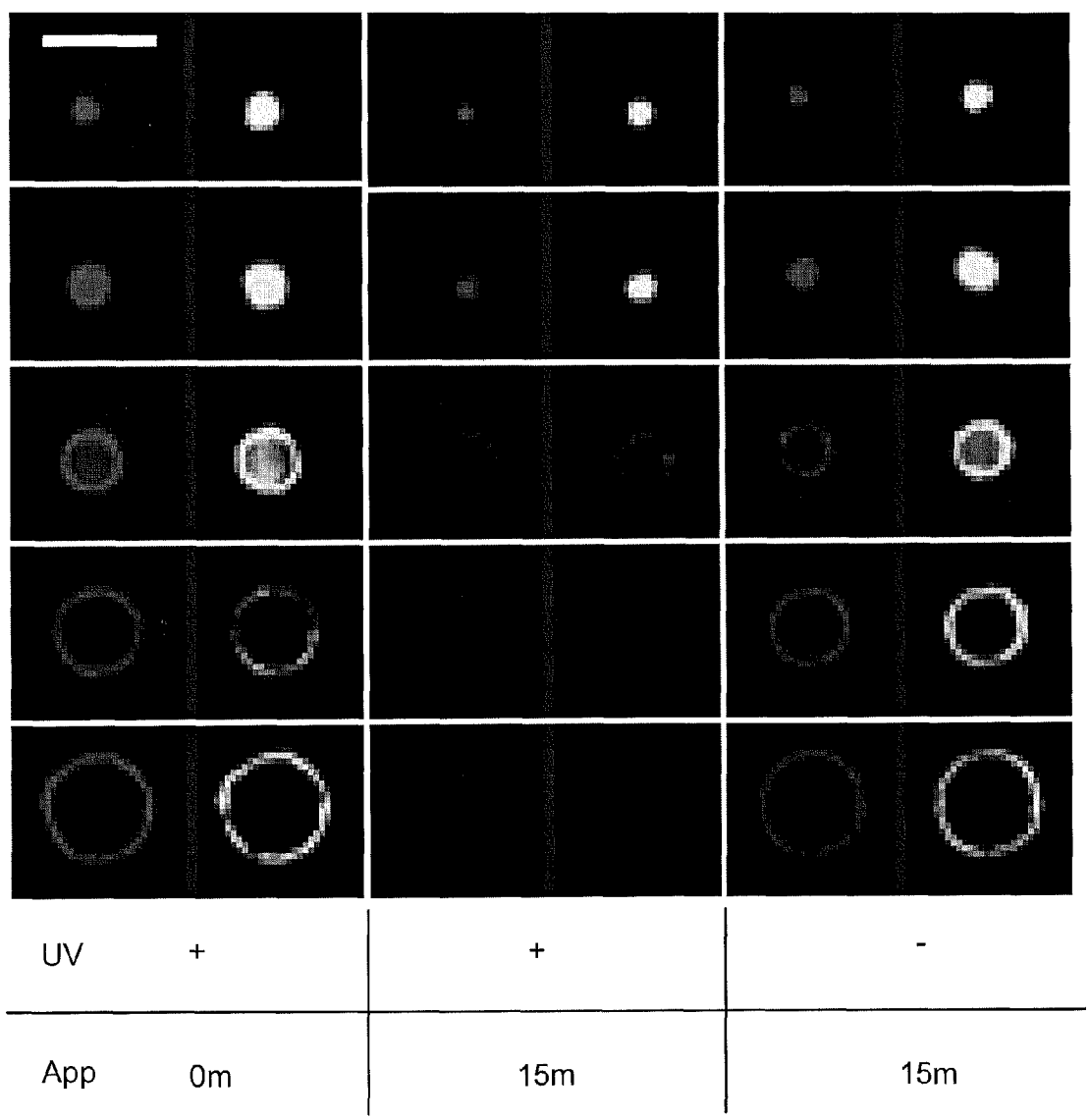
Figure 9B:
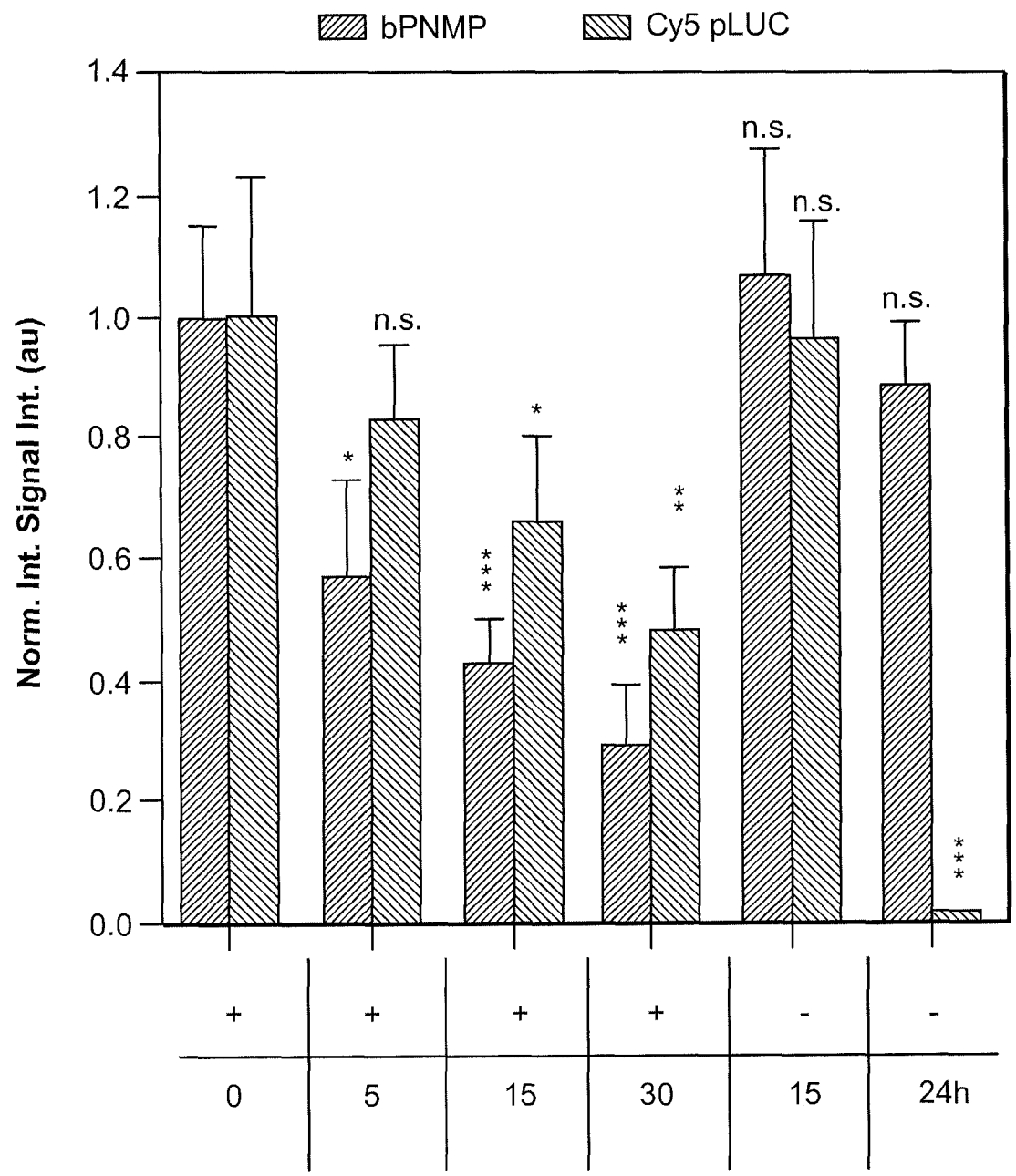

FIG. 9 illustrates that microneedle-based films rapidly delaminate in vitro a, Representative confocal images of an SAv488-bPNMP-(PS/SPS)$_{20}$-(poly-1/Cy5-pLUC)$_{35}$ coated PLLA microneedle with UV treatment, before application (lateral sections, 100 µm interval, scale—200 µm, left, blue—Sav488-bPNMP, yellow—Cy5-pLUC), after 15 min application (middle), and without UV treatment, after 15 min application (right). c, Quantitation of confocal imaging (n=15) showing UV-dependent loss of SAV488-bPNMP and Cy5-pLUC signal upon application to skin.

Figure 10:
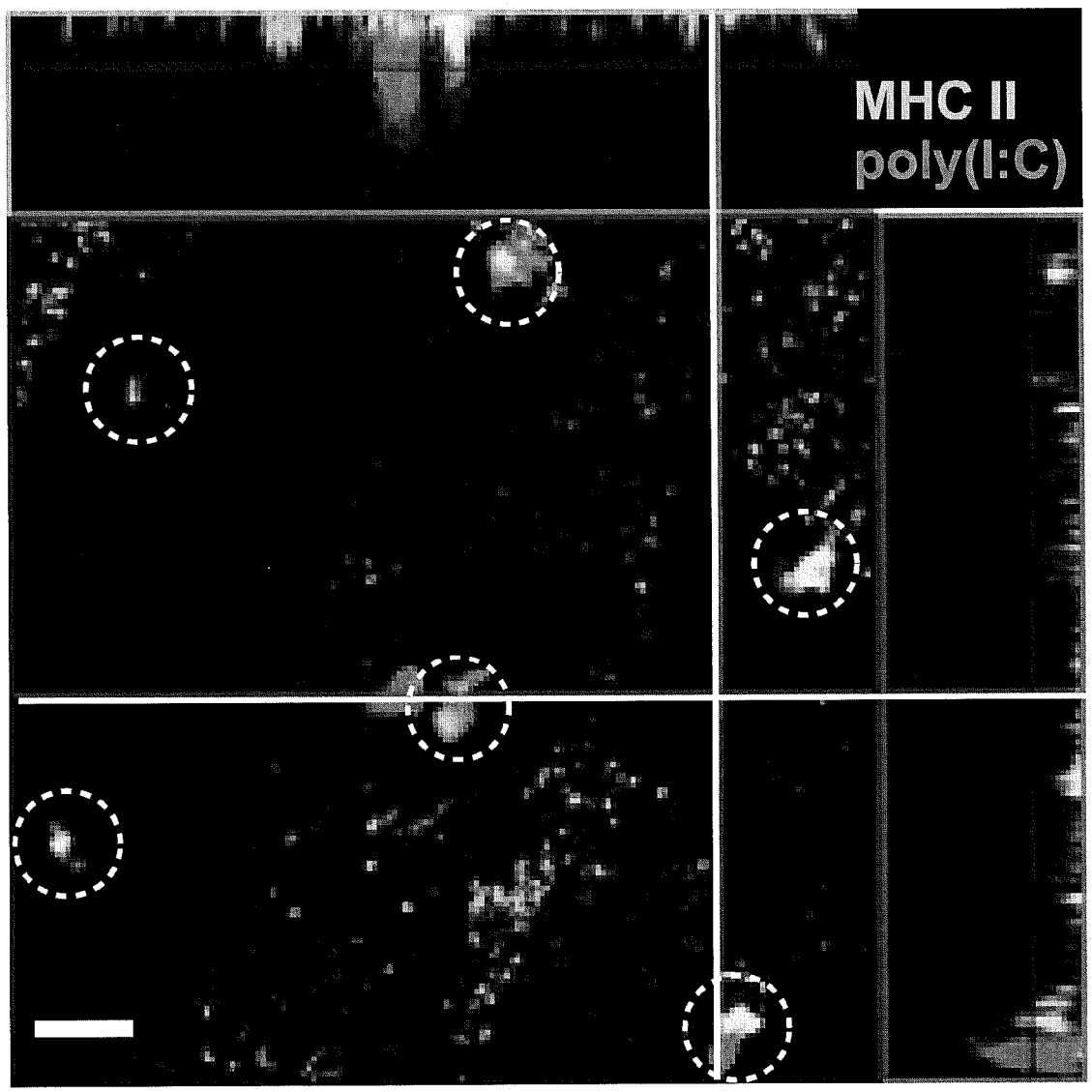

FIG. 10 illustrates that microneedle-based films are rapidly implanted at penetration sites in vivo. a, Representative facial and profile confocal images showing depth of film deposition in treated murine skin after 15 min (green—MHC II-GFP, red—TMR-poly(I:C), penetration site outlined, scale bar—200 µm).

Figure 11:
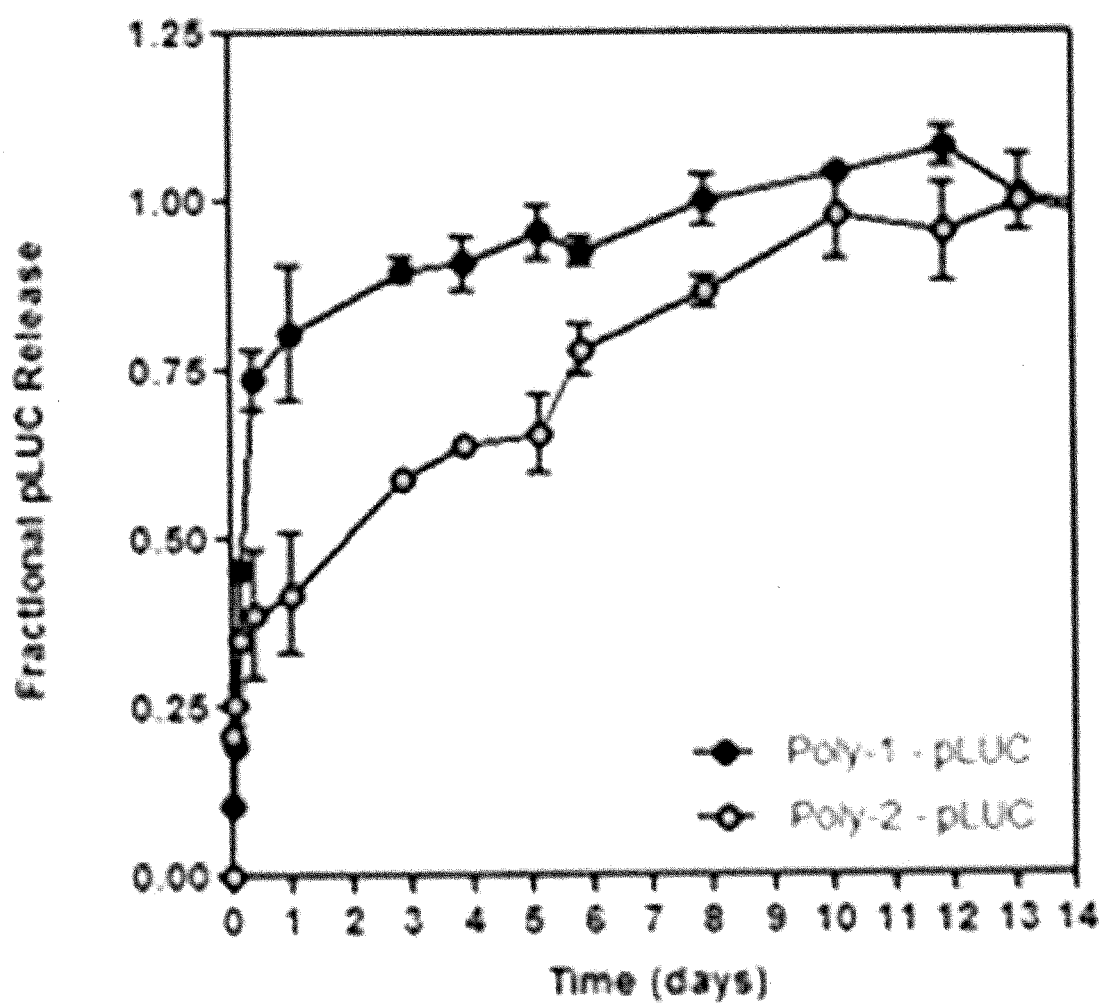

FIG. 11 illustrates that multi-layer films control release of pLUC in vitro. In vitro release of pLUC from (PS/SPS)$_{20}$-(PBAE/pLUC)$_{35}$ films on silicon.

Figure 12A:
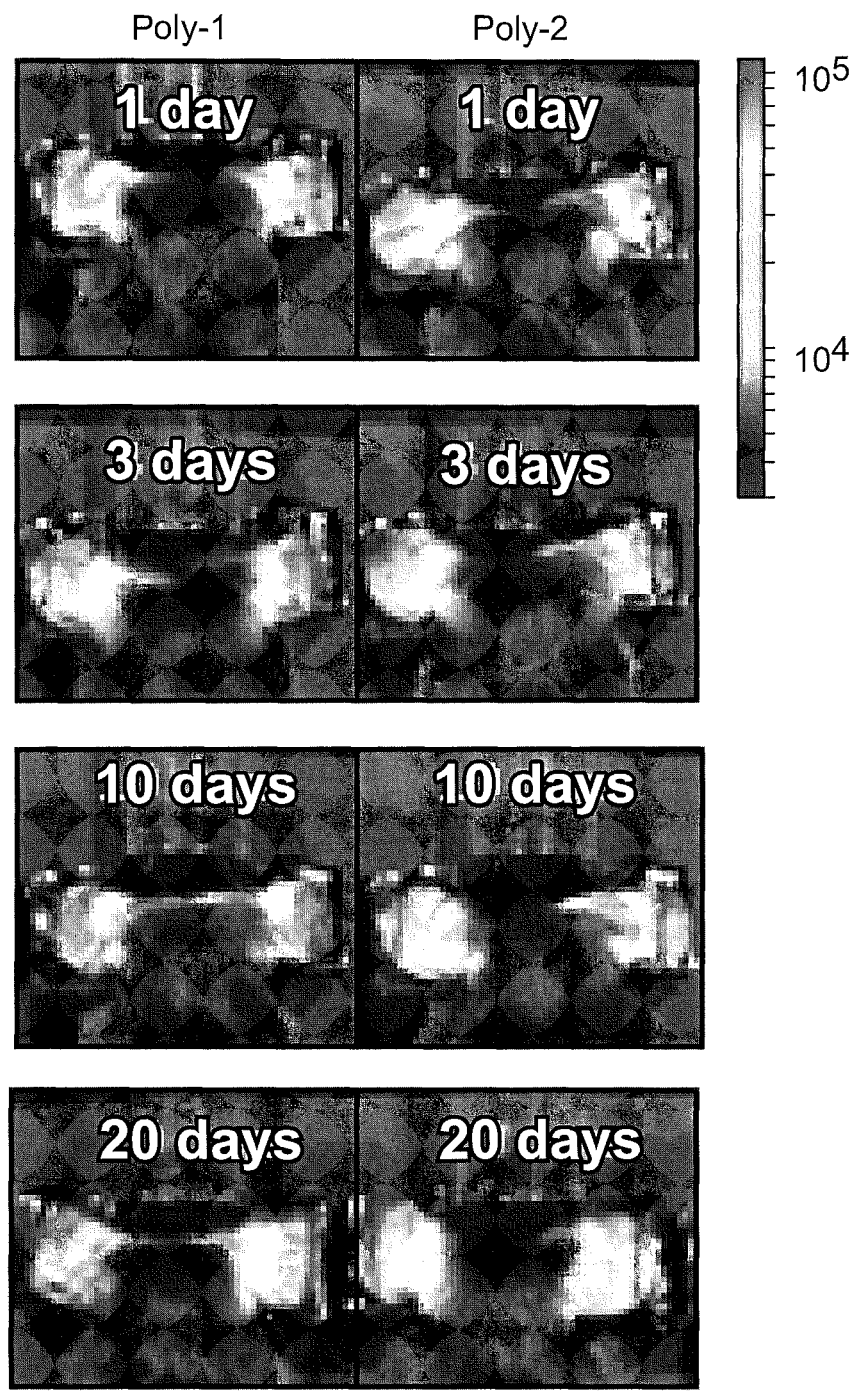
Figure 12B:
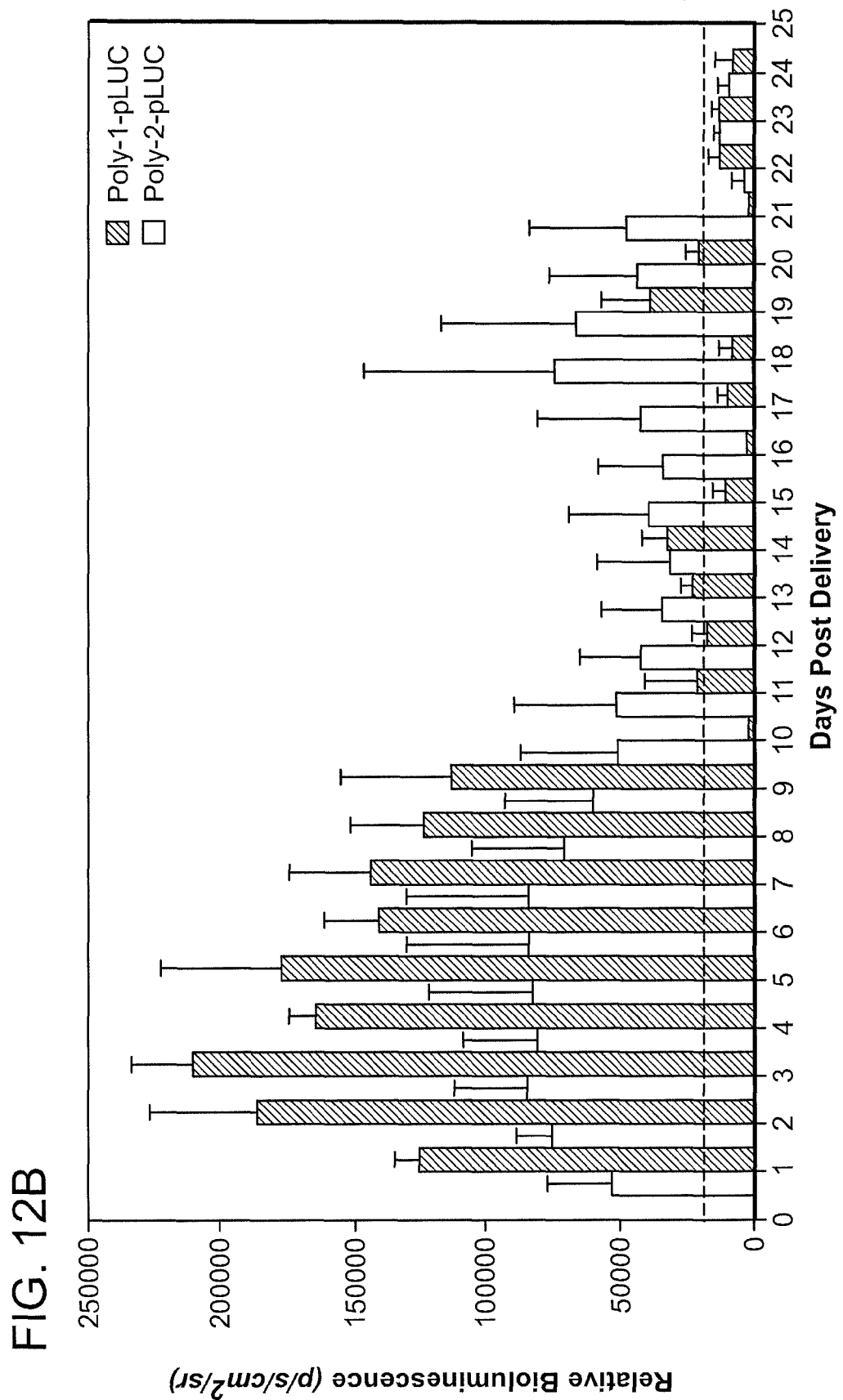

FIG. 12 illustrates that implanted films control and sustain release of pDNA in vivo. Whole animal bioluminescence images of pLUC expression at application site 1, 3, 10, or 20 days following a 15 min application of SAv488-bPNMP-(PS/SPS)$_{20}$-(poly-1/pLUC)$_{35}$ coated microneedle array without UV pretreatment.

Figure 13A:
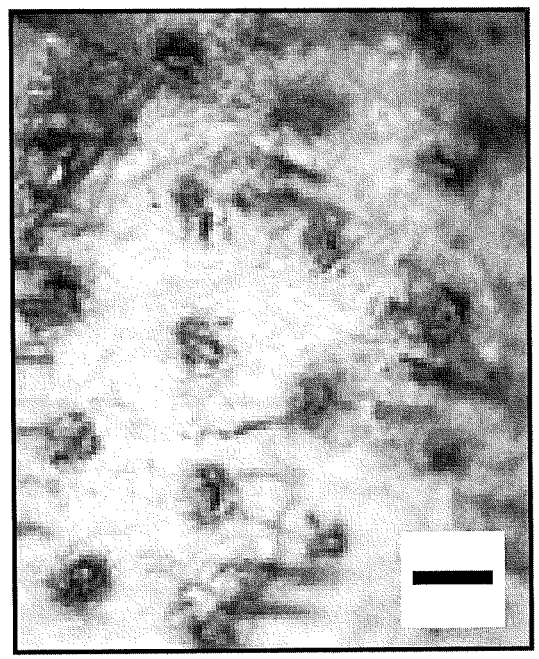
Figure 13B:
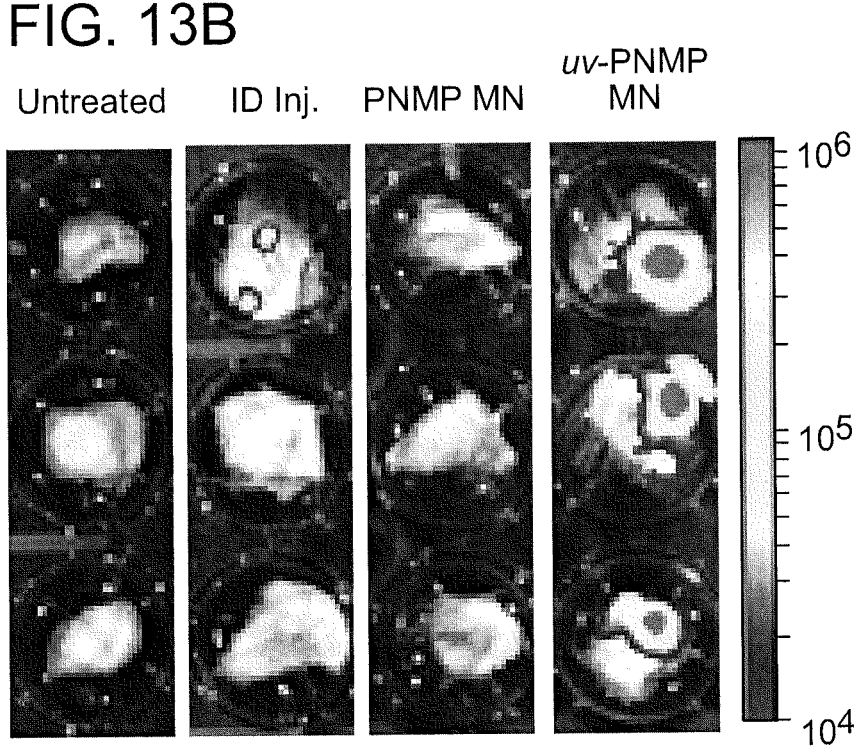

FIG. 13 illustrates that in vitro multi-layer delamination is rapid. Time-lapse optical microscopic images of multi-layer delamination and release from silicon. The delamination of an (LPEI/PAA)$_3$-(BPEI/PAA)$_{30}$ multi-layer film constructed on an underlying uv-PNMP release layer is shown from t=0 (before immersion) to t=30 min (30 min following immersion in PBS at pH 7.4). PBS was added at t=1 sec.

DETAILED DESCRIPTION OF CERTAIN EMBODIMENTS

In various embodiments, compositions and methods for assembling at least one release layer and LBL films associated with one or more agents for delivery are disclosed. Provided film composition and methods can be used to coat a substrate for controlled delivery of one or more agents.

LBL Films

LBL films may have various film architecture, film thickness, film materials, surface chemistry, and/or incorporation of agents according to the design and application of coated devices.

In general, LBL films comprise multiple layers. In many embodiments, LBL films are comprised of multilayer units; each unit comprising individual layers. In accordance with the present disclosure, individual layers in an LBL film interact with one another. In particular, a layer in an LBL film comprises an interacting moiety, which interacts with that from an adjacent layer, so that a first layer associates with a second layer adjacent to the first layer, each contains at least one interacting moiety.

In some embodiments, adjacent layers are associated with one another via non-covalent interactions. Exemplary non-covalent interactions include, but are not limited to, hydrogen bonding, affinity interactions, metal coordination, physical adsorption, host-guest interactions, hydrophobic interactions, pi stacking interactions, hydrogen bonding interactions, van der Waals interactions, magnetic interactions, dipole-dipole interactions and combinations thereof.

In some embodiments, an interacting moiety is a charge, positive or negative. In some embodiments, an interacting moiety is a hydrogen bond donor or acceptor. In some embodiments, an interacting moiety is a complementary moiety for specific binding such as avidin/biotin. In various embodiments, more than one interactions can be involve in the association of two adjacent layers. For example, an electrostatic interaction can be a primary interaction; a hydrogen bonding interaction can be a secondary interaction between the two layers.

LBL films may be comprised of multilayer units with alternating layers of opposite charge, such as alternating anionic and cationic layers.

In some embodiments, the present invention provides the insight that at least some potential layer materials, including potential agents for delivery that could otherwise be utilized as layer materials do not and/or cannot carry sufficient charge to mediate stable electrostatic interactions. In addition to electrostatic interaction or alternatively, they can be associated via non-electrostatic interaction in a coated device in accordance with the present invention.

According to the present disclosure, LBL films may be comprised of one or more multilayer units. In some embodiments, an LBL film may include a plurality of a single unit (e.g., a bilayer unit, a tetralayer unit, etc.). In some embodiments, an LBL film is a composite that includes more than one unit. For example, more than one unit possessing different film architecture (e.g., bilayers, tetralayer, etc.), film thickness, film materials (e.g., polymers), surface chemistry, and/or agents that are associated with one of the units. In some embodiments, an LBL film is a composite that includes more than one bilayer unit, more than one tetralayer unit, or any combination thereof. In some embodiments, an LBL film is a composite that includes a plurality of a single bilayer unit and/or a plurality of a single tetralayer unit.

In some embodiments, the number of a multilayer unit is 3, 5, 10, 20, 30, 40, 50, 60, 70, 80, 90, 100, 150, 200, 300, 400 or even 500.

LBL films may have various thickness depending on design, methods of fabricating, and applications. In some embodiments, an LBL film has an average thickness in a range of about 1 nm and about 100 µm. In some embodiments, an LBL film has an average thickness in a range of about 1 µm and about 50 µm. In some embodiments, an LBL film has an average thickness in a range of about 2 µm and about 5 µm. In some embodiments, the average thickness of an LBL film is or more than about 1 nm, about 100 nm, about 200 nm, about 300 nm, about 400 nm, about 500 nm, about 600 nm, about 700 nm, about 800 nm, about 900 nm, about 1 µm, about 1.5 µm, about 2 µm, about 3 µm, about 4 µm, about 5 µm, about 10 µm, about 20 µm, about 50 µm, about 100 µm. In some embodiments, an LBL film has an average thickness in a range of any two values above.

An individual layer of an LBL film can contain a polymeric material. In some embodiments, a polymer is degradable or non-degradable. In some embodiments, a polymer is natural or synthetic.

In some embodiments, a polymer is a polyelectrolyte.

In some embodiment, a polymer is a polypeptide. In some embodiments, a polymer has a relatively small molecule weight. In some embodiments, a polymer is an agent for delivery. For example, poly-1 and poly-2 were used as transfection agents in Example 1 below.

LBL films can be decomposable. In many embodiments, a polymer of an individual layer includes a degradable polyelectrolyte. In some embodiments, decomposition of LBL films is characterized by substantially sequential degradation of at least a portion of the polyelectrolyte layers that make up the LBL films. Degradation may be at least partially hydrolytic, at least partially enzymatic, at least partially thermal, and/or at least partially photolytic. Degradable polyelectrolytes and their degradation byproducts may be biocompatible so as to make LBL films amenable to use in vivo.

Degradable polyelectrolytes can be used in an LBL film disclosed herein, including, but not limited to, hydrolytically degradable, biodegradable, thermally degradable, and photolytically degradable polyelectrolytes. Hydrolytically degradable polymers known in the art include for example, certain polyesters, polyanhydrides, polyorthoesters, polyphosphazenes, and polyphosphoesters. Biodegradable polymers known in the art, include, for example, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC). Those skilled in the art will recognize that this is an exemplary, not comprehensive, list of biodegradable polymers. Of course, co-polymers, mixtures, and adducts of these polymers may also be employed.

Anionic polyelectrolytes may be degradable polymers with anionic groups distributed along the polymer backbone. Anionic groups, which may include carboxylate, sulfonate, sulphate, phosphate, nitrate, or other negatively charged or ionizable groupings, may be disposed upon groups pendant from the backbone or may be incorporated in the backbone itself. Cationic polyelectrolytes may be degradable polymers with cationic groups distributed along the polymer backbone. Cationic groups, which may include protonated amine, quaternary ammonium or phosphonium-derived functions or other positively charged or ionizable groups, may be disposed in side groups pendant from the backbone, may be attached to the backbone directly, or can be incorporated in the backbone itself.

For example, a range of hydrolytically degradable amine containing polyesters bearing cationic side chains have been developed. Examples of these polyesters include poly(L-lactide-co-L-lysine), poly(serine ester), poly(4-hydroxy-L-proline ester), and poly[α-(4-aminobutyl)-L-glycolic acid].

In addition, poly(β-amino ester)s (PBAE), which can be prepared from the conjugate addition of primary or secondary amines to diacrylates, are suitable for use. Typically, poly(β-amino ester)s have one or more tertiary amines in the backbone of the polymer, preferably having one or two per repeating backbone unit. Alternatively, a co-polymer may be used in which one of the components is a poly(β-amino ester). Poly(β-amino ester)s are described in U.S. Pat. Nos. 6,998,115 and 7,427,394, entitled "Biodegradable poly(β-amino esters) and uses thereof" and Lynn et al., *J. Am. Chem. Soc.* 122:10761-10768, 2000, the entire contents of both of which are incorporated herein by reference.

In some embodiments, a poly(β-amino ester) can have a formula below:

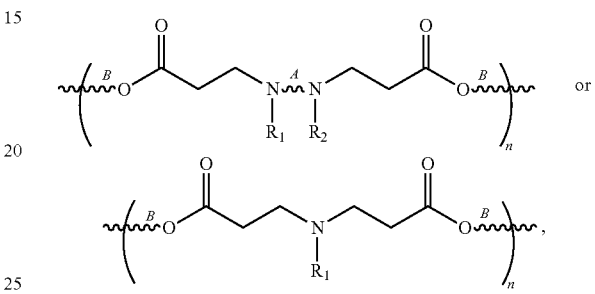

where A and B are linkers which may be any substituted or unsubstituted, branched or unbranched chain of carbon atoms or heteroatoms. The molecular weights of the polymers may range from 1000 g/mol to 20,000 g/mol, preferably from 5000 g/mol to 15,000 g/mol. In certain embodiments, B is an alkyl chain of one to twelve carbons atoms. In other embodiments, B is a heteroaliphatic chain containing a total of one to twelve carbon atoms and heteroatoms. The groups $R_1$ and $R_2$ may be any of a wide variety of substituents. In certain embodiments, $R_1$ and $R_2$ may contain primary amines, secondary amines, tertiary amines, hydroxyl groups, and alkoxy groups. In certain embodiments, the polymers are amine-terminated; and in other embodiments, the polymers are acrylated terminated. In some embodiments, the groups $R_1$ and/or $R_2$ form cyclic structures with the linker A.

Exemplary poly(β-amino esters) include

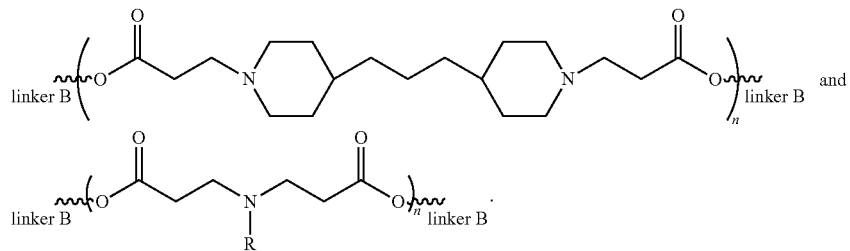

Exemplary R groups include hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups.

Exemplary linker groups B includes carbon chains of 1 to 30 carbon atoms, heteroatom-containing carbon chains of 1 to 30 atoms, and carbon chains and heteroatom-containing carbon chains with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups. The polymer may include, for example, between 5 and 10,000 repeat units.

In some embodiments, poly(β-amino ester)s are selected from the group consisting of can be used. Exemplary non-degradable polyelectrolytes that could be used in thin films include poly(styrene sulfonate) (SPS), poly(acrylic acid) (PAA), linear poly(ethylene imine) (LPEI), poly(diallyldimethyl ammonium chloride) (PDAC), and poly(allylamine hydrochloride) (PAH).

Alternatively or additionally, the degradation rate may be fine-tuned by associating or mixing non-biodegradable, yet biocompatible polymers with one or more of the polyanionic and/or polycationic layers. Suitable non-biodegradable, yet biocompatible polymers are well known in the art and include polystyrenes, certain polyesters, non-biodegradable polyurethanes, polyureas, poly(ethylene vinyl acetate), polypropylene, polymethacrylate, polyethylene, polycarbonates, and poly(ethylene oxide)s.

Polymers used herein in accordance with the present disclosure generally can be biologically derived or natural. Polymers that may be used include charged polysaccharides. In some embodiments, polysaccharides include glycosaminoglycans such as heparin, chondroitin, dermatan, hyaluronic acid, etc. (Some of these terms for glycoasmi-

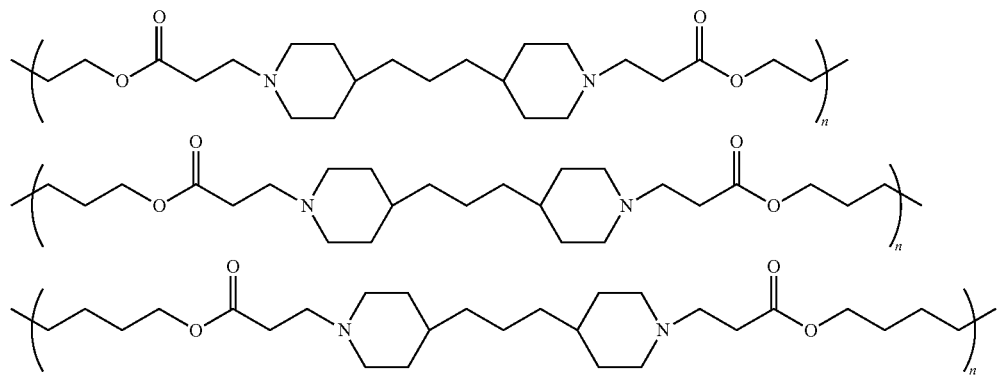

derivatives thereof, and combinations thereof.

Alternatively or additionally, zwitterionic polyelectrolytes may be used. Such polyelectrolytes may have both anionic and cationic groups incorporated into the backbone or covalently attached to the backbone as part of a pendant group. Such polymers may be neutrally charged at one pH, positively charged at another pH, and negatively charged at a third pH. For example, an LBL film may be constructed by LBL deposition using dip coating in solutions of a first pH at which one layer is anionic and a second layer is cationic. If such an LBL film is put into a solution having a second different pH, then the first layer may be rendered cationic while the second layer is rendered anionic, thereby changing the charges on those layers.

The composition of degradable polyeletrolyte layers can be fine-tuned to adjust the degradation rate of each layer within the film, which is believe to impact the release rate of drugs. For example, the degradation rate of hydrolytically degradable polyelectrolyte layers can be decreased by associating hydrophobic polymers such as hydrocarbons and lipids with one or more of the layers. Alternatively, polyelectrolyte layers may be rendered more hydrophilic to increase their hydrolytic degradation rate. In certain embodiments, the degradation rate of a given layer can be adjusted by including a mixture of polyelectrolytes that degrade at different rates or under different conditions.

In other embodiments, polyanionic and/or polycationic layers may include a mixture of degradable and non-degradable polyelectrolytes. Any non-degradable polyelectrolyte noglycans are often used interchangeably with the name of a sulfate form, e.g., heparan sulfate, chondroitin sulfate, etc. It is intended that such sulfate forms are included among a list of exemplary polymers used in accordance with the present invention.).

Additionally or alternatively, polymers can be a natural acid.

LBL films may be exposed to a liquid medium (e.g., intracellular fluid, interstitial fluid, blood, intravitreal fluid, intraocular fluid, gastric fluids, etc.). In some embodiments, an LBL film comprises at least one polycationic layer that degrades and at least one polyanionic layer that delaminates sequentially. Releasable agents are thus gradually and controllably released from the LBL film. It will be appreciated that the roles of the layers of an LBL film can be reversed. In some embodiments, an LBL film comprises at least one polyanionic layer that degrades and at least one polycationic layer that delaminates sequentially. Alternatively, polycationic and polyanionic layers may both include degradable polyelectrolytes.

Release Layer

In accordance with some embodiments of the present disclosure, LBL films can be used with at least one release layer. In many embodiments, at least one release layer and one or more LBL films are assembled and/or deposited on a substrate. When a release layer is removed from a substrate, for example, by dissolution in a liquid medium, LBL films outside the release layer will be released from the substrate. In addition, any other films or layers can be used to coat a substrate. In certain embodiments, those films/layers can be assembled and/or deposited in between a release layer and a substrate, in between a release layer and a LBL film, in between LBL films, or on the most outer film/layer.

In various embodiments, a release layer is or comprises a polymer. Such a polymer, in some embodiments, is stable during deposition/assembly and can be converted to become unstable when exposed in a liquid medium for releasing. In some embodiments, a polymer comprises hydrophobic moieties, which renders the polymer stable and not soluble under certain conditions during its deposition onto a substrate (e.g., a microneedle/microneedle array).

In some embodiments, conversion is conducted by exposing a polymer to UV to photocleave hydrophobic moieties. A polymer can be a photocleavable polymer. A photocleaved polymer can be a pH sensitive polymer, so that the photocleaved polymer is stable at a predetermined pH or in a predetermined pH range, but unstable at or near physiological pH.

In some embodiments, a photocleaved polymer is substantially less soluble in liquid mediums having a predetermined pH and below than in liquid mediums having a pH greater than the predetermined pH. A predetermined pH can be about 5, about 6, about 6.5, about 7, or about 7.4.

In certain embodiments, a terpolymer of a hydrophobic monomer, a hydrophilic monomer, and a monomer having a sidegroup that is photocleavable to produce a carboxyl side chain can be used as a polymer of a release layer in accordance with the present disclosure. To give an example, Poly(o-Nitro benzyl methacrylate-co-Methyl methacrylate-co-Poly(ethylene glycol) methacrylate) (PNMP) was used in Example 1 for the release layer. More details of a terpolymer can be found in US Patent Application No. 20060194145, the contents of which are incorporated herein by reference.

In some embodiments, a terpolymer is a random co-polymer of methyl methacrylate (MMA), poly(ethylene glycol) methacrylate (PEGMA), and o-nitrobenzyl methacrylate (ONBMA). The ratios of the three co-monomers may be adjusted to manipulate the solubility of the terpolymer. In general, sufficient ONBMA may be present to create sufficient carboxylic acid groups after UV exposure to promote solubility. The amount of ONBMA may be at least 30%, at least 35%, at least 40%, at least 45%, or at least 50%. The amount of PEGMA may be adjusted to provide sufficient hydrophilicity that the terpolymer does not dewet from the substrate while not dissolving prematurely in aqueous buffers and to prevent excessive hydrogen bonding between PEGMA and the photogenerated carboxylic acid. The amount of PEGMA will partially depend on the amount of ONBMA and may be 30% or less, 25% or less, 20% or less, 15% or less, or 10% or less. The amount of MMA may be adjusted to provide sufficient hydrophobicity to prevent premature dissolution while not being so great that a terpolymer dewets from substrates. The amount of MMA may be at least at least 30%, at least 35%, at least 40%, at least 45%, or at least 50%. In certain embodiments, PEGMA units also serve as a barrier to nonspecific protein binding to terpolymers.

One skilled in the art will recognize that the composition of the co-monomers may also be varied. Monomers may be substituted for any of MMA, PEGMA, or ONBMA. In general, monomers may be chosen that do not significantly absorb at the wavelength used for cleavage of the photoreactive group. For example, upon UV exposure, the ONBMA is cleaved from a pH sensitive carboxylic acid. The compositions of monomers may be varied using the same considerations (e.g., balancing hydrophobicity and hydrophilicity, minimizing hydrogen bonding, etc.) as described above for the relative ratios of the co-monomers. Exemplary monomers that may be substituted for MMA include ethyl methacrylate, n-butyl methacrylate, n-decyl methacrylate, 2-ethylhexyl methacrylate, N-(n-octadecyl)acrylamide, n-tert-octylacrylamide, stearyl acrylate, stearyl methacrylate, and vinyl stearate. Exemplary monomers that may be substituted for the PEGMA include hydroxyethylmethacrylate, hydroxyethyl acrylate, 4-hydroxybutyl methacrylate, N-(2-hydroxypropyl)methacrylamide, n-methylmethacrylamide, acrylamide, poly(ethylene glycol)monomethyl ether methacrylates, poly(ethylene glycol) methacrylates, and n-vinyl-2-pyrrolidone. The PEG chain on PEGMA may have 6 mers. More or fewer mers may be employed as well, for example, 3-9 mers. A longer PEG chain will increase hydrogen bonding and vice versa.

Alternative photocleavable groups of a general structure

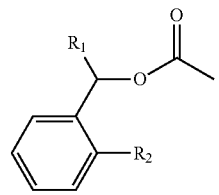

that leave behind a carboxyl group after photocleavage may also be substituted for the o-nitrobenzyl group on the ONBMA. For example, the position $R_2$ may be substituted with benzoyl, hydrogen, benzyl, alkyl, alkenyl, aryl, or cycloalkyl. Three groups may in turn be substituted, for example, with benzoyl, benzyl, alkyl, alkenyl, aryl, or cycloalkyl. Alternatively, or in addition, $R_1$ may be hydrogen or nitro. In one embodiment, benzoin ($R_1$=H, $R_2$=benzoyl), which is photocleavable at 350 nm, is employed. Alternatively or in addition, photocleavage may occur after exposure to about 1350 mJ/cm$^2$ to about 2025 mJ/cm$^2$ or more of UV radiation. One skilled in the art will recognize that the energy required for photocleavage may depend on a variety of factors, including layer composition and thickness. The required energy for a particular layer may be determined by "titrating" the film with various amounts of energy.

The thickness of a release layer may vary depending on methods of deposition and applications. In some embodiments, a release layer has an average thickness in a range of about 1 nm and about 10 µm. In some embodiments, a release layer has an average thickness in a range of about 10 nm and about 1 µm. In some embodiments, a release layer has an average thickness in a range of about 100 nm and about 200 nm. In some embodiments, the average thickness of an LBL film is or more than about 10 nm, about 50 nm, about 80 nm, about 100 nm, about 150 nm, about 200 nm, about 300 nm, about 400 nm, about 500 nm, about 600 nm, about 700 nm, about 800 nm, about 900 nm, about 1 µm, about 5 µm, or about 10 µm. In some embodiments, a release layer has an average thickness in a range of any two values above.

Agents for Delivery

Film compositions and/or film-coated substrates utilized in accordance with the present invention can comprise one or more agents for delivery. In some embodiments, one or more agents are independently associated with a substrate, an LBL film coating the substrate, or both in a coated substrate.

In some embodiments, an agent can be associated with individual layers of an LBL film for incorporation, affording the opportunity for exquisite control of loading and release from the film. In certain embodiments, an agent is incorporated into an LBL film by serving as a layer.

In some embodiments, an agent for delivery is released when one or more layers of a LBL film are decomposed. Additionally or alternatively, an agent is released by diffusion.

In theory, any agents may be associated with the LBL film disclosed herein to be released, which includes, for example, therapeutic agents (e.g. antibiotics, NSAIDs, glaucoma medications, angiogenesis inhibitors, neuroprotective agents), cytotoxic agents, diagnostic agents (e.g. contrast agents; radionuclides; and fluorescent, luminescent, and magnetic moieties), prophylactic agents (e.g. vaccines), transfection agents, immunological agents (e.g., adjuvant), nutraceutical agents (e.g. vitamins, minerals, etc.), and/or other substances that may be suitable for introduction to biological tissues, including pharmaceutical excipients and substances for tattooing, cosmetics, and the like.

In some embodiments, an agent can be small molecules, large (i.e., macro-) molecules, or a combination thereof. Exemplary agents include, but are not limited to, small molecules (e.g. cytotoxic agents), nucleic acids (e.g., siRNA, RNAi, and microRNA agents), proteins (e.g. antibodies), peptides, lipids, carbohydrates, hormones, metals, radioactive elements and compounds, drugs, vaccines, transfection agents, immunological agents, etc., and/or combinations thereof. In some embodiments, an agent can be a drug formulation including various forms, such as liquids, liquid solutions, gels, hydrogels, solid particles (e.g., microparticles, nanoparticles), or combinations thereof.

In some embodiments, compositions and methods in accordance with the present disclosure are particularly useful for vaccination and/or therapeutic by releasing of one or more nucleic acids. In certain embodiments, a nucleic acid is a plasmid DNA.

In addition to nucleic acids or alternatively, various other agents may be associated with compositions in accordance with the present disclosure. In some embodiments, transfection agents and/or immunological agents can be used in combination with nucleic acids. In certain embodiments, a transfection agent is a cationic polymer. For example, poly (β-amino ester) (PBAE) as discussed herein can be used as a transfection agent. In certain embodiments, an immunological agent is an adjuvant molecule (e.g., poly(I:C) as used in Example 1).

Compositions in many embodiments of the present disclosure can comprise therapeutic agents for delivery. In some embodiments, a therapeutic agent is a small molecule and/or organic compound with pharmaceutical activity. In some embodiments, a therapeutic agent is a clinically-used drug. In some embodiments, a therapeutic agent to be delivered is an agent useful in combating inflammation and/or infection. In some embodiments, a therapeutic agent is or comprises an antibiotic, anti-viral agent, anesthetic, anticoagulant, anti-cancer agent, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, etc.

In some embodiments, a therapeutic agent may be a mixture of pharmaceutically active agents. For example, a local anesthetic may be delivered in combination with an anti-inflammatory agent such as a steroid. Local anesthetics may also be administered with vasoactive agents such as epinephrine. To give but another example, an antibiotic may be combined with an inhibitor of the enzyme commonly produced by bacteria to inactivate the antibiotic (e.g., penicillin and clavulanic acid).

In some embodiments, a therapeutic agent may be an antibiotic. Exemplary antibiotics include, but are not limited to, β-lactam antibiotics, macrolides, monobactams, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, bacitracin, erythromycin, nalidixic acid, vancomycin, and trimethoprim. For example, β-lactam antibiotics can be ampicillin, aziocillin, aztreonam, carbenicillin, cefoperazone, ceftriaxone, cephaloridine, cephalothin, cloxacillin, moxalactam, penicillin G, piperacillin, ticarcillin and any combination thereof.

In some embodiments, a therapeutic agent may be an anti-inflammatory agent. Anti-inflammatory agents may include corticosteroids (e.g., glucocorticoids), cycloplegics, non-steroidal anti-inflammatory drugs (NSAIDs), immune selective anti-inflammatory derivatives (ImSAIDs), and any combination thereof. Exemplary NSAIDs include, but not limited to, celecoxib (Celebrex®); rofecoxib (Vioxx®), etoricoxib (Arcoxia®), meloxicam (Mobic®), valdecoxib, diclofenac (Voltaren®, Cataflam®), etodolac (Lodine®), sulindac (Clinori®), aspirin, alclofenac, fenclofenac, diflunisal (Dolobid®), benorylate, fosfosal, salicylic acid including acetylsalicylic acid, sodium acetylsalicylic acid, calcium acetylsalicylic acid, and sodium salicylate; ibuprofen (Motrin), ketoprofen, carprofen, fenbufen, flurbiprofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldene®), indomethacin (Indocin®), nabumetone (Relafen®), naproxen (Naprosyn®), tolmetin, lumiracoxib, parecoxib, licofelone (ML3000), including pharmaceutically acceptable salts, isomers, enantiomers, derivatives, prodrugs, crystal polymorphs, amorphous modifications, co-crystals and combinations thereof.

Those skilled in the art will recognize that this is an exemplary, not comprehensive, list of agents that can be released using compositions and methods in accordance with the present disclosure.

Substrate

A coated device in accordance with the present invention comprises one or more multilayer films coated on at least one surface of a substrate.

A variety of materials can be used as a substrate. In some embodiments, a material of a substrate is metals (e.g., gold, silver, platinum, and aluminum); metal-coated materials; metal oxides; and combinations thereof. In some embodiments, a material of a substrate is plastics, ceramics, silicon, glasses, mica, graphite or combination thereof. In some embodiments, a material of a substrate is a polymer. Exemplary polymers include, but are not limited to, polyamides, polyphosphazenes, polypropylfumarates, polyethers, polyacetals, polycyanoacrylates, polyurethanes, polycarbonates, polyanhydrides, polyorthoesters, polyhydroxyacids, polyacrylates, ethylene vinyl acetate polymers and other cellulose acetates, polystyrenes, poly(vinyl chloride), poly(vinyl fluoride), poly(vinyl imidazole), poly(vinyl alcohol), poly (ethylene terephthalate), polyesters, polyureas, polypropylene, polymethacrylate, polyethylene, poly(ethylene oxide)s and chlorosulphonated polyolefins; and combinations thereof. In some embodiments, a substrate may comprise more than one material to form a composite.

A substrate can be a medical device. Some embodiments of the present disclosure comprise various medical devices, such as sutures, bandages, clamps, valves, intracorporeal or extracorporeal devices (e.g., catheters), temporary or permanent implants, stents, vascular grafts, anastomotic devices, aneurysm repair devices, embolic devices, and implantable devices (e.g., orthopedic implants) and the like.

Microneedle Substrates

Microneedle substrates, for example, can be used in accordance with the present invention. Coated microneedle substrates and methods for coating are described herein, enabling various multilayer films containing agents to be controllably coated onto microneedle substrates. Such coated microneedle substrates can be contacted with biological tissues, particularly for transdermal delivery of agents.

In some embodiments, a microneedle substrate is provided which includes at least one microneedle having a base, a tip end, and a shaft portion therebetween, and a multilayer film coating on at least a portion of the surface of the microneedle. In some embodiments, the multilayer film coating includes at least one releasable agents. Such multilayer film coatings can be a homogeneous or a heterogeneous composition.

A microneedle substrate can be formed/constructed of different biocompatible materials, including metals, glasses, semi-conductor materials, ceramics, or polymers. Examples of suitable metals include pharmaceutical grade stainless steel, gold, titanium, nickel, iron, tin, chromium, copper, and alloys thereof. In some embodiments, stainless steel is an attractive material for microneedle fabrication because it is FDA approved for medical devices and is inexpensive.

In some embodiments, a microneedle substrate may include or be formed of a polymer. A polymer can be biodegradable or non-biodegradable. Examples of suitable biocompatible, biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes and copolymers and blends thereof. Representative non-biodegradable polymers include polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof. Biodegradable microneedles can provide an increased level of safety compared to non-biodegradable ones, such that they are essentially harmless even if inadvertently broken off into the biological tissue following contact.

In some embodiments, a microneedle substrate includes a substantially planar foundation from which one or more microneedles extend, typically in a direction normal (i.e., perpendicular or 'out-of-plane') to the foundation. Additionally or alternatively, microneedles may be fabricated on the edge of a substrate 'in-plane' with the substrate. In some embodiments, a single microneedle can be fabricated on a substrate surface or edge. In some embodiments, microneedles are fabricated on a flexible base substrate. It would be advantageous in some circumstances to have a base substrate that can bend to conform to the shape of the surface of a biological tissue in which the substrate contacts. In some embodiments, the microneedles are fabricated on a curved base substrate. The curvature of the base substrate typically would be designed to conform to the shape of the tissue surface.

Microneedles in theory can be of any shape or design. A microneedle may be solid or hollow. A microneedle can be porous or non-porous. A microneedles may be planar, cylindrical, or conical.

In some embodiments, the dimensions of a microneedle, or array thereof, are designed for the particular way in which it is to be used. In various embodiments, the microneedle may have a dimension in a range of between about 50 μm and about 5000 μm, about 100 μm and about 1500 μm, or between about 200 μm and about 1000 μm.

In some embodiments, a microneedle substrate includes a single microneedle or an array of two or more microneedles. The microneedles can be fabricated as, or combined to form microneedle arrays. For example, a microneedle substrate may include an array of between 2 and 1000 (e.g., between 2 and 100) microneedles. In some embodiments, a microneedle substrate may include an array of between 2 and 10 microneedles. An array of microneedles may include a mixture of different microneedles. For instance, an array may include microneedles having various lengths, base portion diameters, tip portion shapes, spacings between microneedles, drug coatings, etc.

Methods and Uses

There are several advantages to LBL assembly techniques used to coat a substrate in accordance with the present disclosure, including mild aqueous processing conditions (which may allow preservation of biomolecule function); nanometer-scale conformal coating of surfaces; and the flexibility to coat objects of any size, shape or surface chemistry, leading to versatility in design options. According to the present disclosure, one or more LBL films in addition to at least one release layer can be assembled and/or deposited on a substrate to provide a coated device.

In many embodiments, a coated device having one or more agents for delivery associated within LBL films, such that decomposition of layers of LBL films results in release of the agents. LBL films can be different in film architecture (e.g., bilayers, tetralayer, etc.), film thickness, film materials (e.g., polymers), surface chemistries, and/or agent association depending on methods and/or uses. In many embodiments, a coated device in accordance with the present disclosure is for medical use.

It will be appreciated that an inherently charged surface of a substrate can facilitate LBL assembly of an LBL film on the substrate. In addition, a range of methods are known in the art that can be used to charge the surface of a substrate, including but not limited to plasma processing, corona processing, flame processing, and chemical processing, e.g., etching, micro-contact printing, and chemical modification.

In some embodiments, a substrate can be coated with a base layer. Additionally or alternatively, substrates can be primed with specific polyelectrolyte bilayers such as, but not limited to, LPEI/SPS, PDAC/SPS, PAH/SPS, LPEI/PAA, PDAC/PAA, and PAH/PAA bilayers, that form readily on weakly charged surfaces and occasionally on neutral surfaces. Exemplary polymers can be used as a primer layer include poly(styrene sulfonate) and poly(acrylic acid) and a polymer selected from linear poly(ethylene imine), poly(diallyl dimethyl ammonium chloride), and poly(allylamine hydrochloride). It will be appreciated that primer layers provide a uniform surface layer for further LBL assembly and are therefore particularly well suited to applications that require the deposition of a uniform thin film on a substrate that includes a range of materials on its surface, e.g., an implant or a complex tissue engineering construct.

The assembly/deposition of release layers and LBL films can be performed separately. In some embodiments, assembly/deposition of multilayer films may involve a series of dip coating steps in which a substrate is dipped in alternating solutions. In some embodiments, assembly/deposition of multilayer films may involve mixing, washing or incubation steps to facilitate interactions of layers, in particular, for non-electrostatic interactions. Additionally or alternatively, it will be appreciated that assembly/deposition of multilayer films may also be achieved by spray coating, dip coating, brush coating, roll coating, spin casting, or combinations of any of these techniques. In some embodiments, spray coating is performed under vacuum. In some embodiments, spray coating is performed under vacuum of about 10 psi, 20 psi, 50 psi, 100 psi, 200 psi or 500 psi. In some embodiments, spray coating is performed under vacuum in a range of any two values above.

In some embodiments, a release layer is deposited on a substrate and then converted to alter its property to become releasable under certain conditions. For example, conversion can be conducted by exposing a release layer to UV. Such a step of converting can be performed before or after the step of assembling LBL films.

Certain characteristics of a coated device may be modulated to achieve desired functionalities for different applications. Dose (e.g., loading capacity) may be modulated, for example, by changing the number of multilayer units that make up the film, the type of degradable polymers used, the type of polyelectrolytes used, and/or concentrations of solutions of agents used during construction of LBL films. Similarly, release kinetics (both rate of release and release timescale of an agent) may be modulated by changing any or a combination of the aforementioned factors.

In some embodiments, the total amount of agent released per square centimeter is about or greater than about 1 mg/cm$^2$. In some embodiments, the total amount of agent released per square centimeter in an LBL film is about or more than about 100 μg/cm$^2$. In some embodiments, the total amount of agent released per square centimeter in an LBL film is about or more than about 50 μg/cm$^2$. In some embodiments, the total amount of agent released per square centimeter in an LBL film is about or more than about 10 mg/cm$^2$, about 1 mg/cm$^2$, 500 μg/cm$^2$, about 200 μg/cm$^2$, about 100 μg/cm$^2$, about 50 μg/cm$^2$, about 40 μg/cm$^2$, about 30 μg/cm$^2$, about 20 μg/cm$^2$, about 10 μg/cm$^2$, about 5 μg/cm$^2$, or about 1 μg/cm$^2$. In some embodiments, the total amount of agent released per square centimeter in an LBL film is in a range of any two values above.

Release of a releasable agent may follow linear kinetics over a period of time. Release of multiple drugs from a multilayer film may be complicated by interactions between layers, and/or drugs. Such a release profile may be desirable to effect a particular dosing regimen. During all or a part of the time period of release, release may follow approximately linear kinetics.

A release timescale (e.g., $t_{50\%}$, $t_{85\%}$, $t_{99\%}$) of an agent for delivery can vary depending on applications. In some embodiments, a release timescale of an agent for delivery is less or more than about 1 hour, 2 hours, 3 hours, 4 hours, 5 hours, 10 hours, 15 hours, 20 hours, 25 hours, 30 hours, 40 hours, 50 hours, 75 hours, 100 hours, 150 hours, or 200 hours. In some embodiments, a release timescale of an agent for delivery is less or more than about 1 day, 2 days, about 5 days, about 10 days, about 12 days, about 20 days, about 30 days, 50 or about 100 days. In some embodiments, a release timescale of an agent for delivery is in a range of any two values above.

EXAMPLES

Example 1

In this Example, rapid hypodermic-needle-free DNA delivery was demonstrated, using microneedle patches that implant multi-layer polymer films into the epidermis following a brief application to skin. Biodegradable multi-layer films carrying DNA, a polymeric transfection agent, and adjuvant molecules implanted in murine skin both efficiently transfected cells in the local tissue and elicited immune responses comparable to in vivo electroporation of plasmid DNA (pDNA), one of the most promising current technologies for DNA vaccine delivery.

Figure 1A:
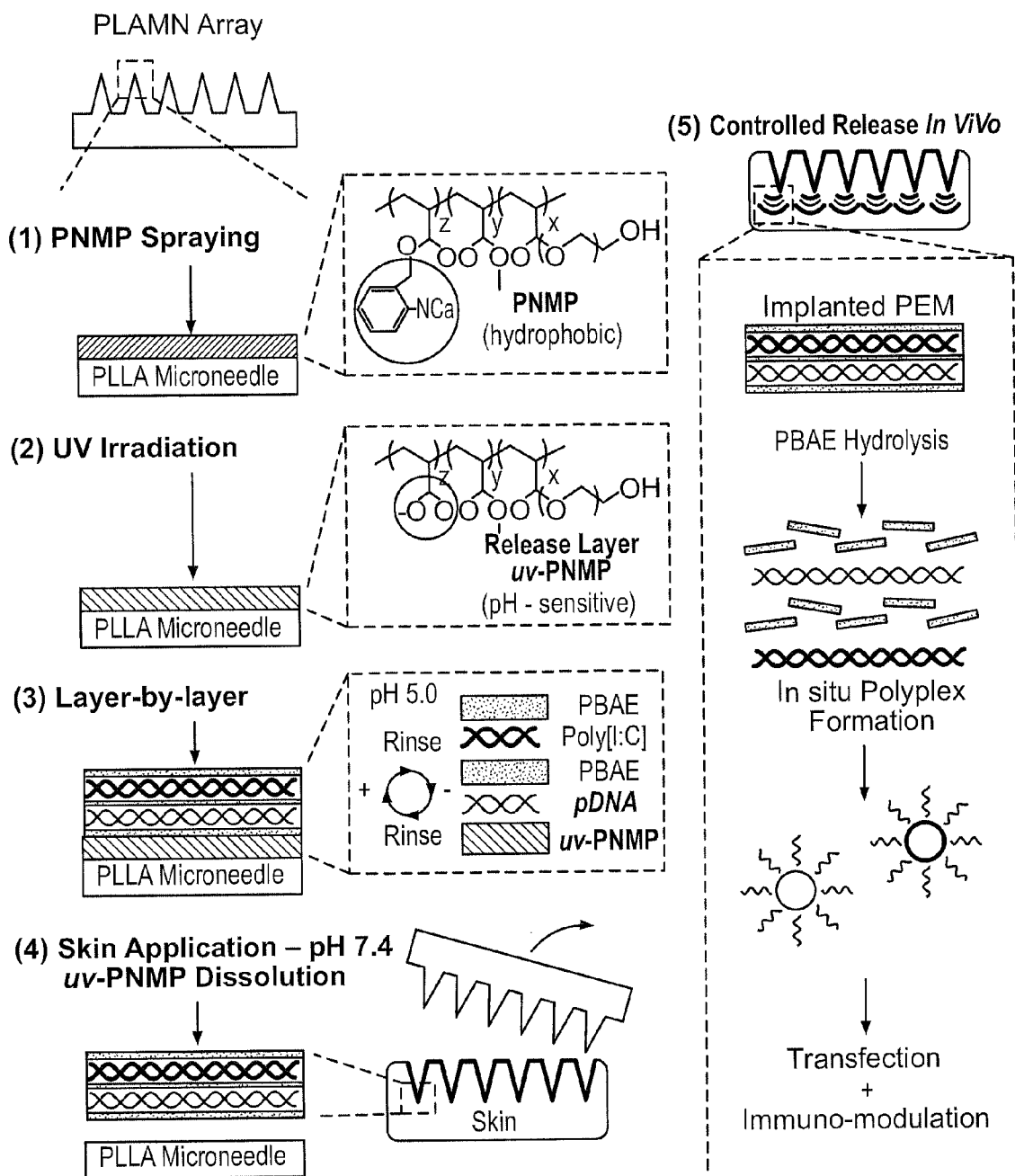
FIG. 1 illustrates quick-release multi-layer film architecture and rapid delamination behavior. a, (1) PLLA microneedles are coated with PNMP through spraying in 1,4-dioxane. (2) UV-irradiation converts PNMP from hydrophobic to hydrophilic with pH-sensitive dissolution behavior, forming a uv-PNMP 'release-layer'. (3) Overlying multi-layer films are constructed using LbL at pH 5.0. (4) Microneedle application to skin and exposure to pH 7.4 gives rapid release-layer dissolution, mediating overlying film delamination and implantation following array removal. (5) Implanted films provide controlled/sustained release through hydrolytic PBAE degradation forming polyplexes for transfection and immune-modulation. b, Micrograph and surface profilometer trace showing heterogeneous film architecture for silicon-based $(LPEI/PAA)_3$-$(BPEI/PAA)_{30}$ films, with an underlying uv-PNMP release layer (arrow, scale bar—100 µm). c, Time-lapse micrographs showing release-layer dissolution and multi-layer delamination following exposure to PBS, pH 7.4. Shown are micrographs for 1, 4, and 30 minutes incubation (scale bar—500 µm).

To substantially enhance DNA vaccine delivery, an approach was designed to simultaneously (i) improve targeting of DNA to tissues rich in immune response-governing dendritic cells, (ii) promote sustained transfection without toxicity, (iii) and provide supporting inflammatory cues to enhance the induction of a potent immune response. To this end, a strategy was developed using microneedles to rapidly and painlessly implant biodegradable drug delivery films into the skin, which continuously released DNA polyplexes and adjuvant molecules in this immunologically-rich tissue over a tunable and sustained period of time (FIG. 1a). Relative to other potential materials that might achieve this goal, PolyElectrolyte Multi-layers (PEMs) have a number of advantages including their ability to be assembled by mild aqueous processing, easily embed diverse cargos in their nanostructure, carry large weight fractions of functional cargo (e.g., DNA, up to 40% of total film mass), and exhibit controlled release characteristics predetermined by film architecture/composition. In addition, PEMs composed of nucleic acids and polymeric transfection agents have been previously been demonstrated to transfect cells in vitro and in vivo, through the continuous release of in situ-formed polyplexes.

To translate this concept in vivo for vaccination, an approach for polymer multi-layer "tattooing" was developed using microneedle arrays coated with vaccine-loaded PEMs that are released from the microneedle surface and remain implanted into the skin as the patch is removed (FIG. 1a). It is contemplated here that multi-layer release can be achieved via an underlying polymeric 'release layer' designed to instantly dissolve on hydration by interstitial fluid in the skin (FIG. 1a). This design allows the kinetics of DNA/adjuvant release in the tissue to be separately tailored from the time required for a microneedle patch to be kept on the skin. However, a water-soluble release layer would by definition be unstable during aqueous Layer-by-Layer (LBL) coating of the microneedle array with the vaccine multi-layer. To solve this problem, we employed a photo-sensitive polymer, Poly(o-Nitro benzyl methacrylate-co-Methyl methacrylate-co-Poly(ethylene glycol) methacrylate) (PNMP) for the release layer (FIG. 1a). PNMP is organic soluble, but on brief exposure to UV, cleavage of the pendant o-nitrobenzyl groups converts the polymer to a weak polyelectrolyte (uv-PNMP) that is soluble in water above pH~6.5 but stable in aqueous solutions below this pH. It is demonstrated here that the organic solubility of PNMP permitted facile deposition on microneedles by spray deposition from volatile organic solvents, while the selective water solubility of uv-PNMP allowed both aqueous LBL assembly of an overlying PEM from mildly acidic pH buffers and rapid release of the PEM when dried films were exposed to near-neutral pH solutions. Further, as shown below, photo-switchable PNMP solubility provided the means to prove that PEM film implantation depended on release layer dissolution.

Figure 1B:
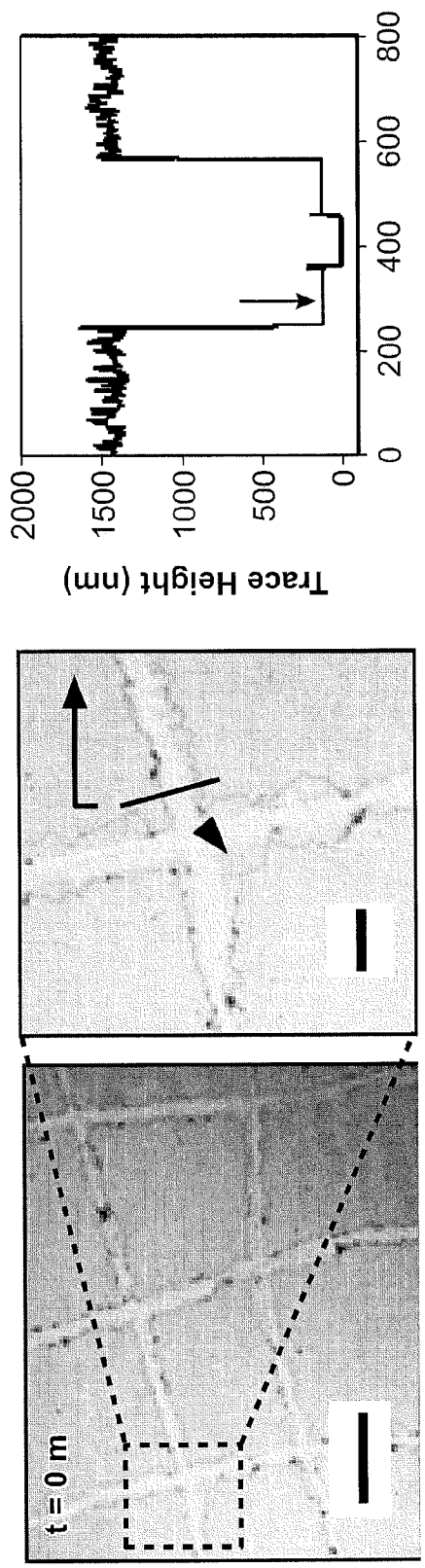
Figure 1C:
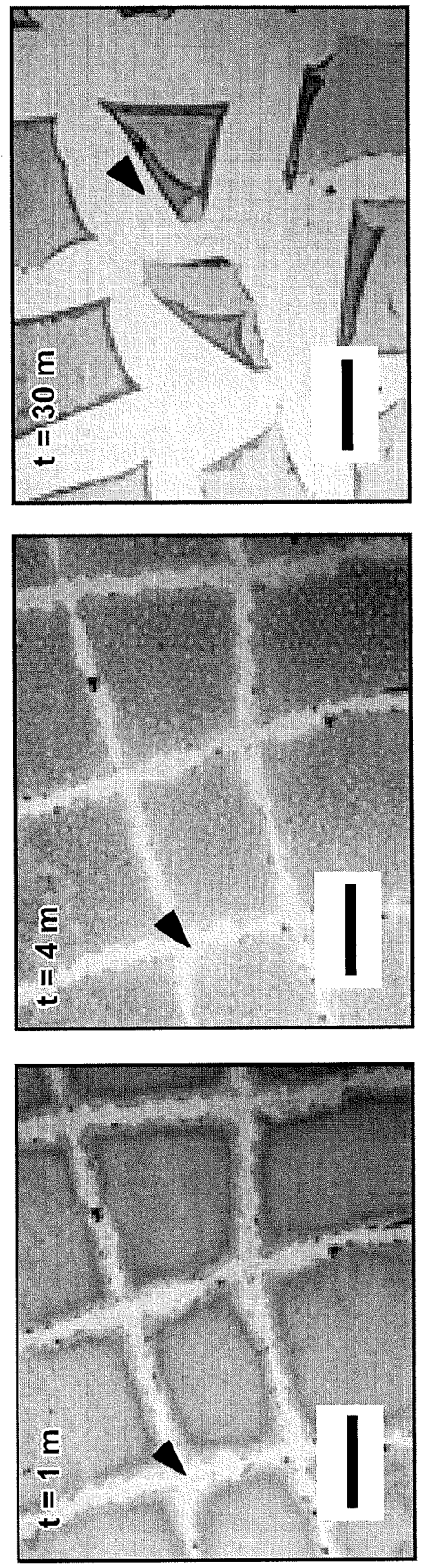

To first demonstrate the use of PNMP copolymer coatings to serve as a pH-responsive base for PEM assembly and subsequent release from an underlying substrate, the PNMP thin films (130 nm in thickness) were cast on silicon, UV-irradiated to induce the organic-to-aqueous solubility transition in the polymer, and then constructed overlying model PEM films composed of linear poly(ethyleneimine) (LPEI)/poly(acrylic acid) (PAA) and branched PEI (BPEI)/ PAA bilayers using LBL assembly from aqueous polymer solutions at pH 5. After scratching ~1500 nm thick dried (PNMP)-(LPEI/PAA)$_3$(BPEI/PAA)$_{30}$ films with a razor blade, the underlying intact PNMP release layer could be directly observed by light microscopy, and surface profilometry at the edge of these defects showed that the thickness of the underlying uv-PNMP layer was unchanged (131±3 nm) following (PEI/PAA)$_3$-(BPEI/PAA)$_{30}$ film deposition (FIG. 1b). Next, the film-coated substrates were immersed in pH 7.4 phosphate-buffered saline (PBS) and observed by time-lapse optical microscopy. The uv-PNMP layer was observed to dissolve within 1 min of exposure to PBS, followed by the formation and coalescence of aqueous bubbles under the PEM film and macroscopic delamination of intact films without any agitation after approximately 15 min (FIG. 1c and FIG. 13). Physical agitation greatly accelerated this process, with delamination observed nearly instantaneously following immersion of dry films and agitation by pipetting (not shown). Multi-layer delamination was dependent upon UV exposure of the PNMP prior to PEM assembly and the pH of the immersion buffer, as no PNMP dissolution or film delamination was observed for composite films that did not receive UV pre-treatment or that were incubated in buffered solutions at pH<6.5 (data not shown).

Figure 2B:
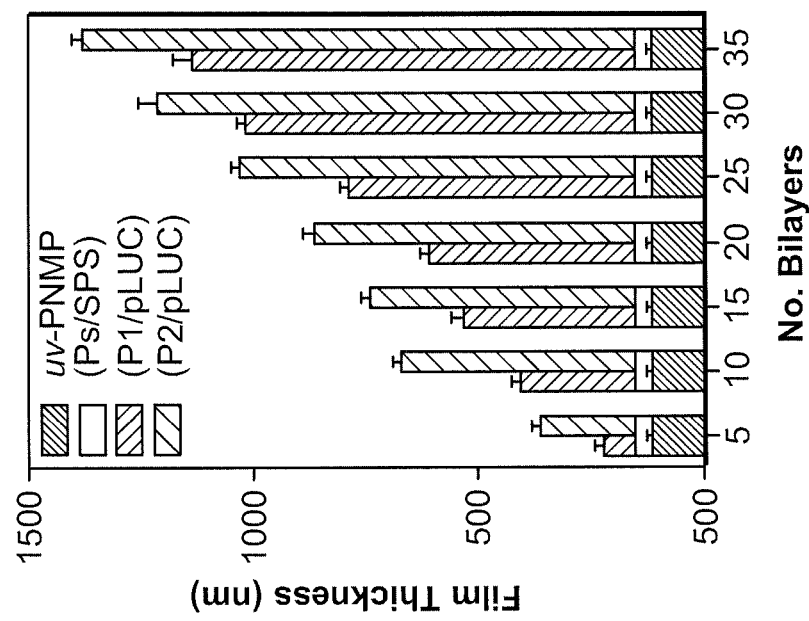
FIG. 2 illustrates that multi-layer film deposition is controllable and modular. a, Film architecture for uv-PNMP-$(PS/SPS)_{20}$-$(PBAE/pLUC)_n$ multi-layers. b, Film growth for $(poly-1/pLUC)_n$ and $(poly-2/pLUC)_n$ multi-layers assembled following uv-PNMP and $(PS/SPS)_{20}$ deposition on silicon. Shown is the thickness of the underlying uv-PNMP release layer, and the overlying (PS/SPS), and $(PBAE/pLUC)_n$ films. c, Representative confocal images of a SAv488-bPNMP-$(PS/SPS)_{20}$-$(poly-1/Cy5-pLUC)_{35}$ coated PLLA microneedles (left—transverse sections, right—lateral sections, 100 µm interval, scale—200 µm, blue—Sav488-uv-bPNMP, yellow—Cy5-pLUC). d, Quantification of encapsulated Cy5-pLUC and Sav488-bPNMP in PLLA microneedle-based SAv488-bPNMP-$(PS/SPS)_{20}$-$(poly-1/Cy5-pLUC)_n$ films through confocal image analysis (left axis, n=15) and total film elution (right axis, n=3). e, Film architecture for uv-PNMP-$(PS/SPS)_{20}$-$(Poly-1/pLUC)$-$(Poly-1/poly(I:C))$ multi-layers. f, Representative confocal images of SAv488-uv-bPNMP-$(PS/SPS)_{20}$-$(poly-1/TMR-poly(I:C))_{15}$-$(poly-1/Cy5-pLUC)_{15}$ coated PLLA microneedle (left—transverse sections, right—lateral sections, 100 µm interval, scale—200 µm, blue—Sav488-uv-bPNMP, yellow—Cy5-pLUC, red—TMR-poly(I:C)). g, Quantification of encapsulated Cy5-pLUC, TMR-poly(I:C), and SAv488-bPNMP in PLLA microneedle-based SAv488-bPNMP-$(PS/SPS)_{20}$-$(poly-1/TMR-poly(I:C))_n$-$(poly-1/Cy5-pLUC)_n$ films through confocal image analysis (n=15) and h, total film elution (right axis, n=3).
Figure 2A:
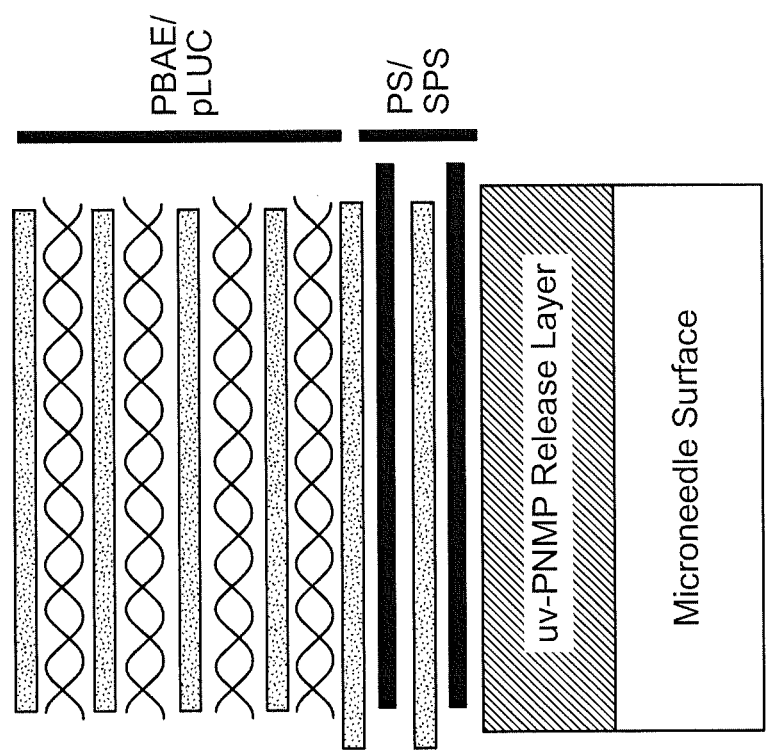
Figure 2D:
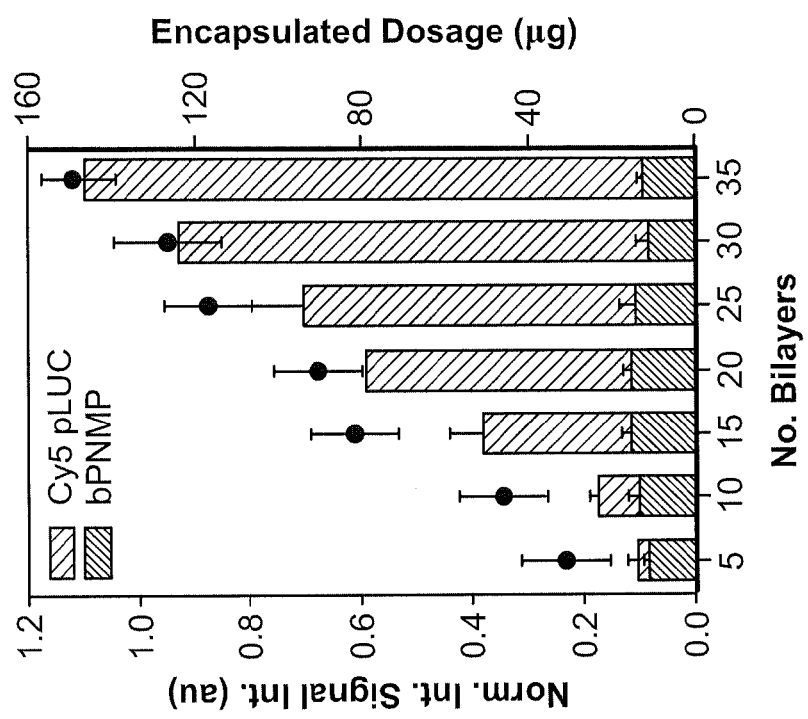
Figure 2C:
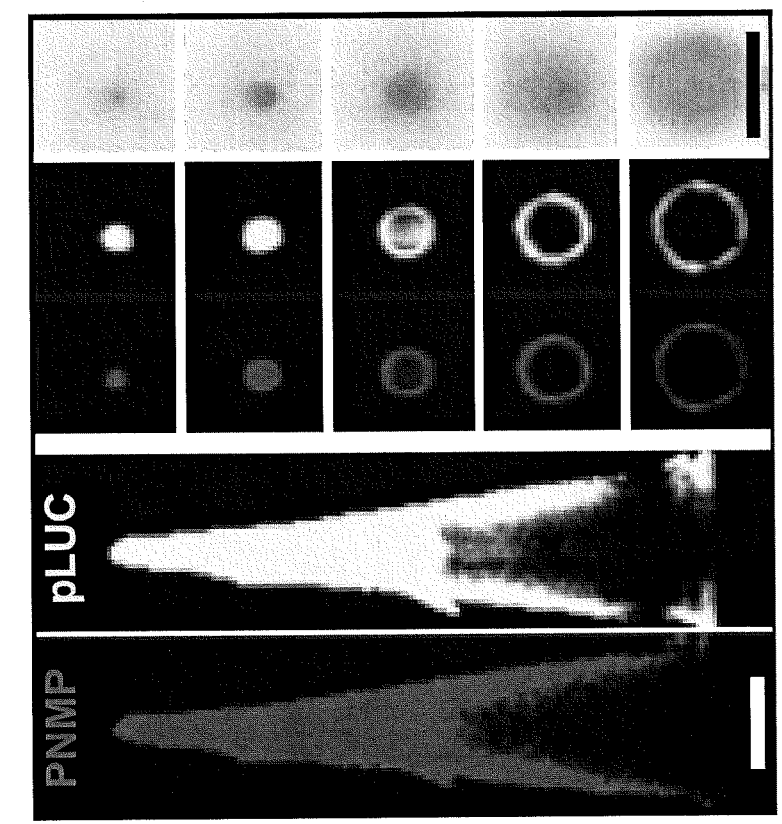
Figure 2E:
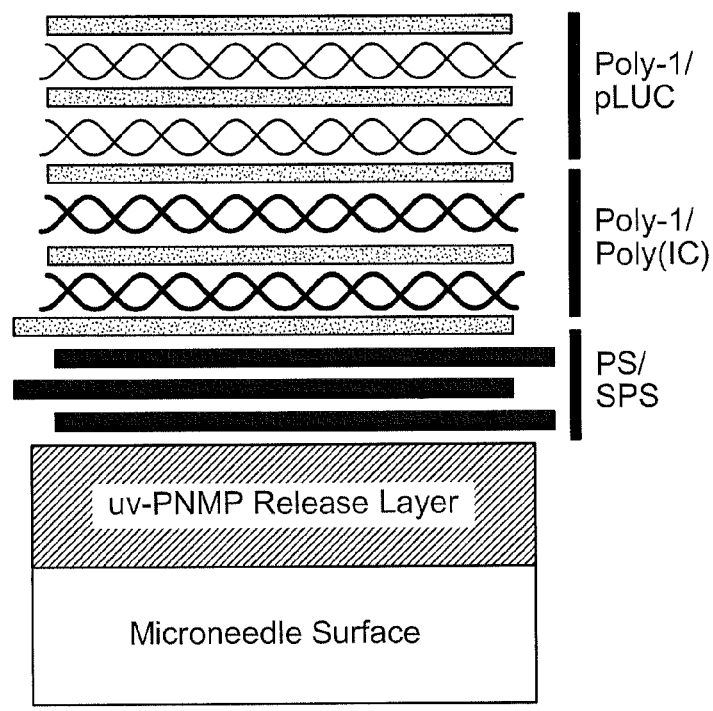
Figure 2F:
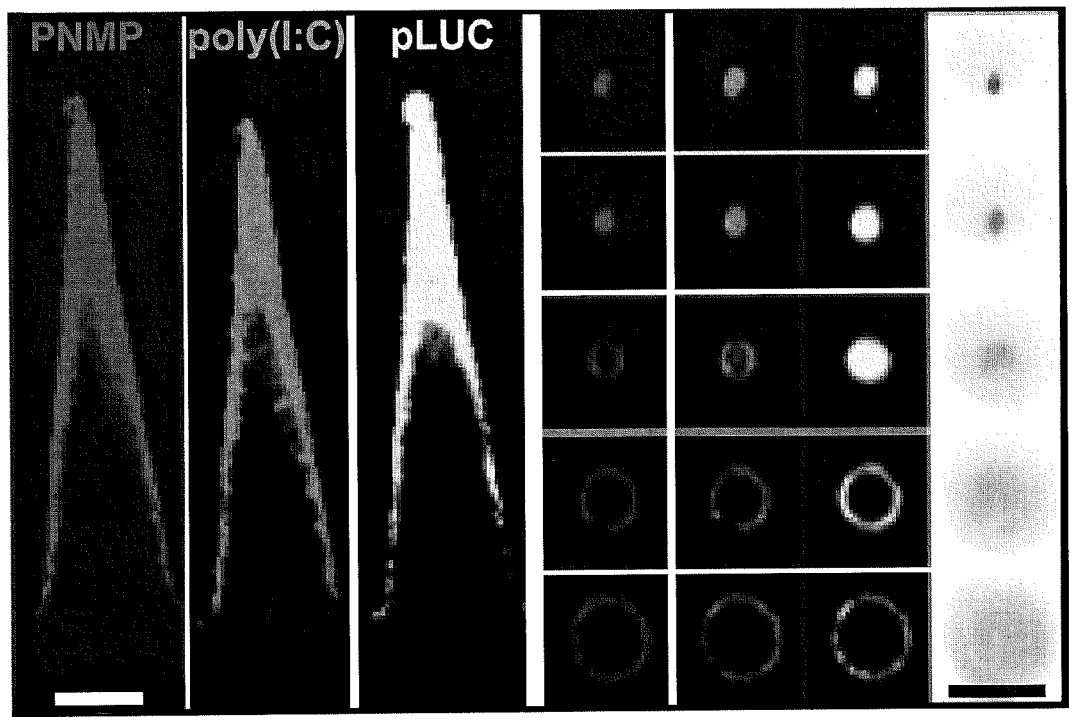
Figure 2G:
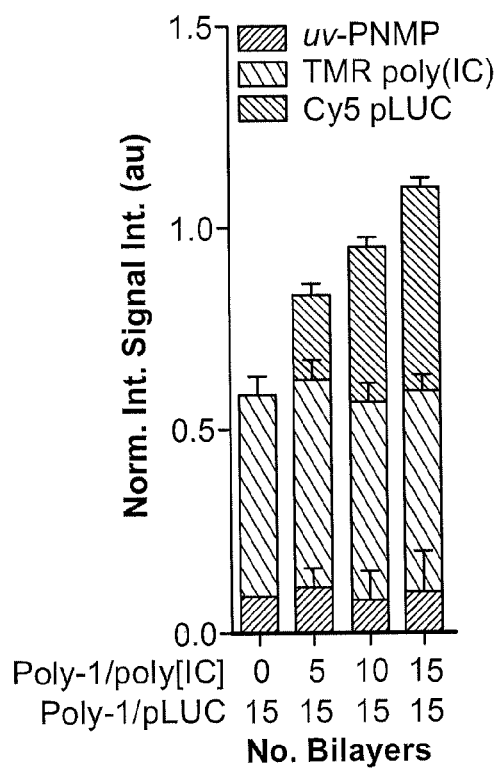
Figure 2H:
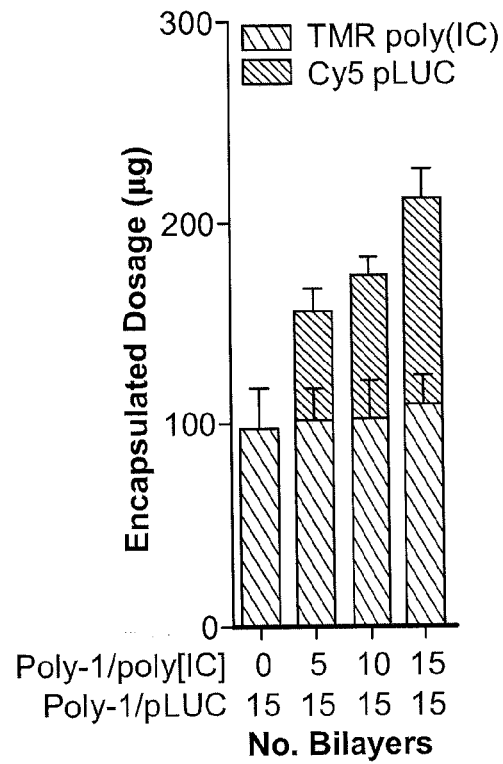

Given these promising initial results, an analogous process was developed for fabrication of microneedle arrays coated with PNMP release layers underlying a DNA vaccine-carrying PEM film. Skin patches were first fabricated by melt-molding poly(L-lactide) (PLLA) on poly(dimethyl siloxane) (PDMS) masters to obtain arrays of microneedles each 250 µm in diameter at their base and 650 µm in height (FIG. 6). Biotinylated PNMP (bPNMP), (FIG. 7) films were coated on the microneedles by spray deposition from 1,4-dioxane solutions, followed by staining with fluorescent streptavidin (SAv488) to permit visualization of the release layer by microscopy. Next, LBL deposition was used to construct an overlying PEM film composed of Cy5-labeled pDNA encoding luciferase (Cy5-pLUC) and the transfection agent poly-1 (FIG. 7), a biodegradable poly(β-amino ester) (PBAE). PEM films were initiated by depositing 20 bilayers of protamine sulfate (PS) and poly(4-styrene sulfonate) (PSS) to provide a uniform charge density, followed by iterative adsorption of poly-1 and Cy5-pLUC (FIG. 2a). Profilometry measurements performed on PEMs constructed in parallel on Si substrates showed linear multi-layer growth with increasing deposition cycles as previously reported for PBAE/pDNA films and intact underlying uv-PNMP films (FIG. 2b). Cross-sectional confocal imaging of microneedles coated with composite uv-PNMP-(poly-1/ Cy5-pLUC)$_{35}$ PEM films showed conformal co-localized fluorescence from SAv-labeled uv-bPNMP and Cy5-pLUC over the surface of each PLLA microneedle (FIG. 2c). (Individual uv-bPNMP and PEM films were too thin to resolve as distinct layers). When analyzed at each stage of PEM film deposition, the mean total SAv488-bPNMP fluorescence signal from single microneedles was stable but Cy5-pLUC fluorescence linearly increased with each round of bilayer deposition, confirming linear film growth on the microneedles as well (FIG. 2d). In line with this result, the total dosage of DNA recovered from microneedle coatings disrupted by treatment with sodium chloride showed a linear increase in plasmid dosage with increasing bilayer number (~4.2 µg/bilayer per cm$^2$ microneedle array area, FIG. 2d). Similar analyses of microneedles coated with PNMP and multi-layers comprised of poly-1 or poly-2 and the nucleic acid adjuvant poly(I:C) also showed conformal film deposition and approximately linear film growth with increasing number of deposited bilayers (FIG. 8). Finally, sequential assembly of PEM films comprising layers of (poly-1/poly (I:C)) followed by layers of (poly-1/pLUC) generated microneedles coated with complete vaccine films containing pDNA, a transfection agent, and a strong adjuvant (FIG. 2e-h and FIG. 8).

To test PEM film release from microneedle arrays, dried composite SAv-labeled uv-bPNMP-(PS/SPS)$_{20}$(poly-1/ Cy5-pLUC)$_{35}$ coatings (referred to henceforth as PNMP/ PEM films) were immersed in pH 7.4 PBS for varying times in vitro and imaged by confocal microscopy to quantitate uv-bPNMP and Cy5-pLUC fluorescence remaining on the microneedle surfaces over time. Mirroring the results obtained with model films on flat Si substrates, we observed a significant loss of both SAv488-uv-bPNMP and Cy5-pLUC fluorescence from microneedle arrays after only 15 min incubation in PBS without agitation (FIG. 9). Delamination plateaued after 30 min with approximately 60% loss of both SAv488-uv-bPNMP and Cy5-pLUC signal. By contrast, no film release was observed if PEMs were assembled onto PNMP coatings that had not been irradiated to photo-switch the release layer's solubility. However, in agreement with our previous report of biodegradable (poly-1/pDNA) microneedle coatings, composite films prepared without UV-treatment of the release layer showed complete loss of Cy5-pLUC signal due to hydrolysis of poly-1 and degradation of the PEM by 24 hr, while the SAv488-uv-bPNMP signal remained unchanged (FIG. 9). Thus, DNA-carrying PEM films assembled onto a pH-sensitive PNMP release layer are rapidly released from the surfaces of microneedles when exposed to physiological saline solution, coincident with rapid PNMP film dissolution.

Figure 3A:
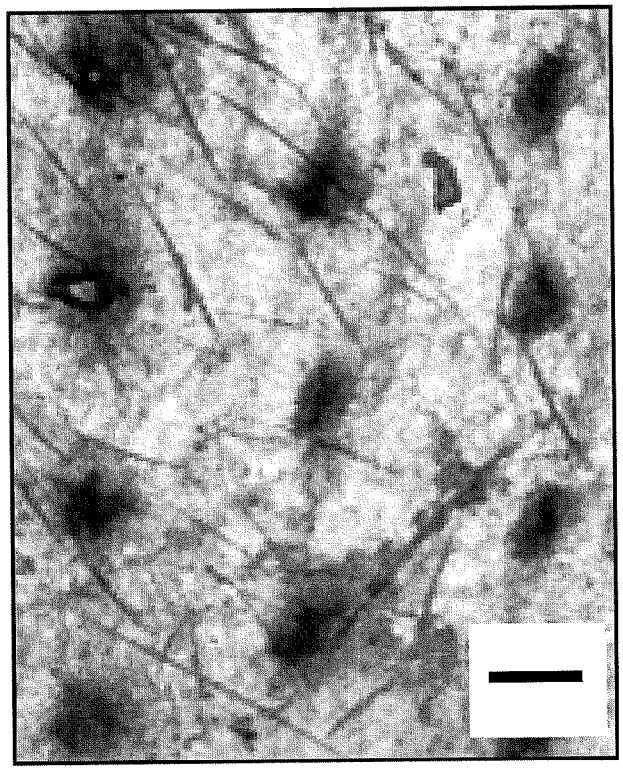
FIG. 3 demonstrates that microneedle-based films are rapidly implanted at penetration sites in vivo. a, Optical micrograph of ear skin showing microneedle penetration pattern stained using trypan blue (scale bar—500 µm). b, Quantitation of confocal imaging (n=15) showing UV-dependent loss of Sav488-bPNMP and Cy5-pLUC signal upon application to skin. c, Representative confocal images of an SAv488-bPNMP-$(PS/SPS)_{20}$-$(poly-1/Cy5-pLUC)_{35}$ coated PLLA microneedle with UV treatment, before application (lateral sections, 100 µm interval, scale—200 µm, left, blue—Sav488-bPNMP, yellow—Cy5-pLUC), after 15 min application (middle), and without UV treatment, after 15 min application (right). d, Representative confocal image of treated murine skin showing film implantation after 15 min (green—MHC II-GFP, yellow—Cy5-pLUC, penetration site outlined, scale bar—100 µm). e, Facial and profile confocal images showing depth of Cy5-pLUC film deposition after 15 minute microneedle application (green—MHC II-GFP, yellow—Cy5-pLUC, penetration site outlined, scale bar—200 µm). f, Representative confocal image of treated murine skin showing TMR-poly(I:C) film implantation after 15 minute microneedle application (green—MHC II-GFP, red—TMR-poly(I:C), penetration site outlined, scale bar—100 µm)). g, Colocalization and uptake of TMR-poly(I:C) by MHC II-GFP$^+$ APCs at microneedle insertion site 24 hrs following film implantation (green—MHC II-GFP, red—TMR-poly(I:C), yellow—overlay, scale bar—50 µm)). ***, $p<0.0001$, analyzed by unpaired t-test
Figure 3B:
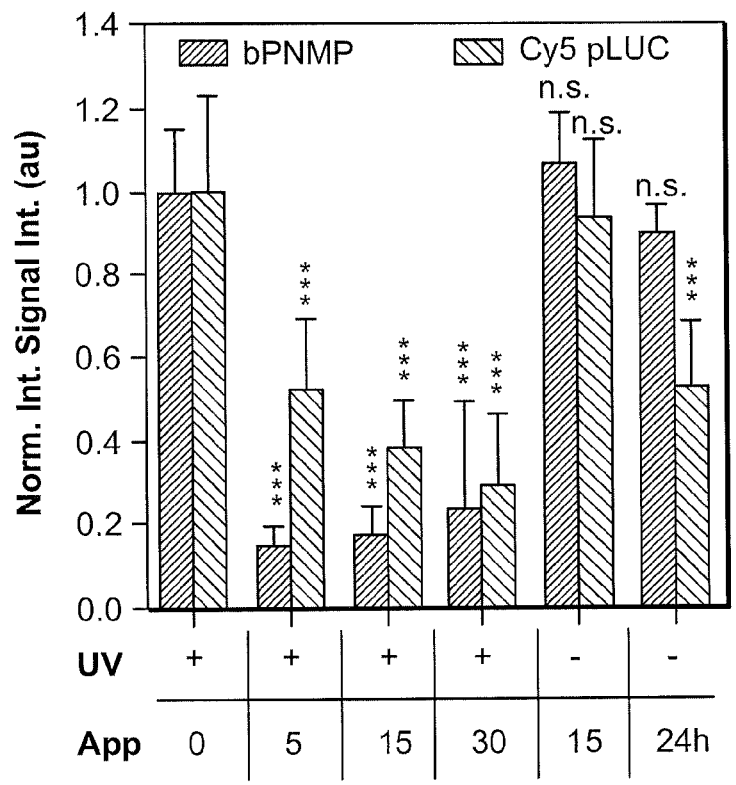
Figure 3C:
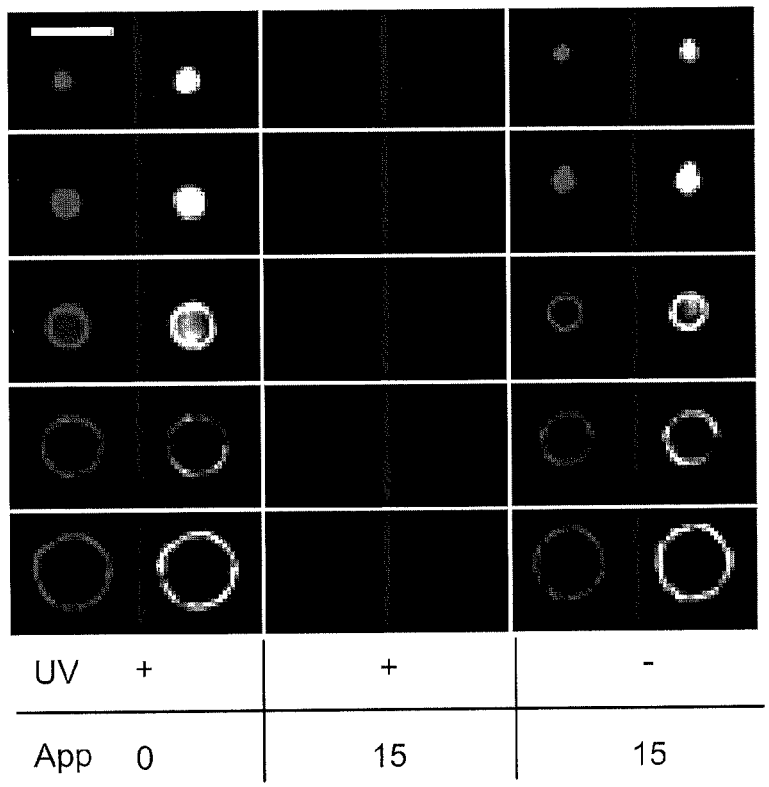
Figure 3D:
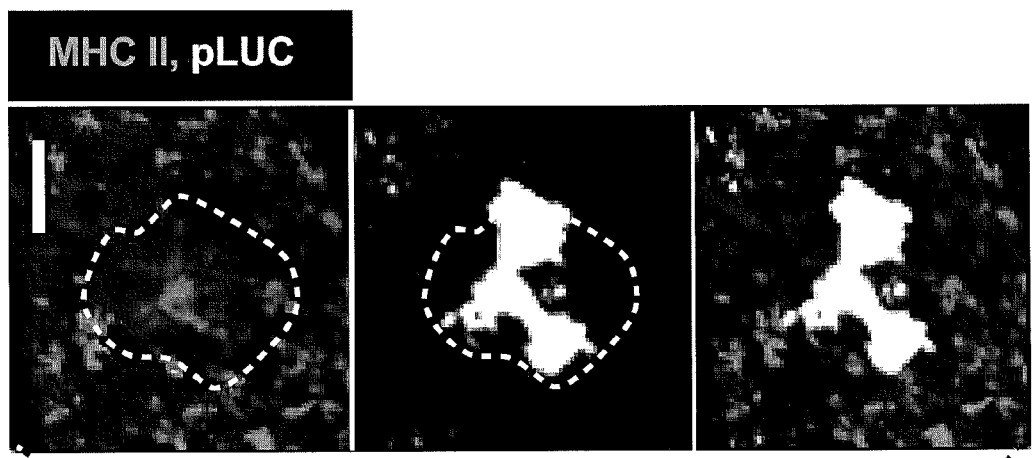
Figure 3E:
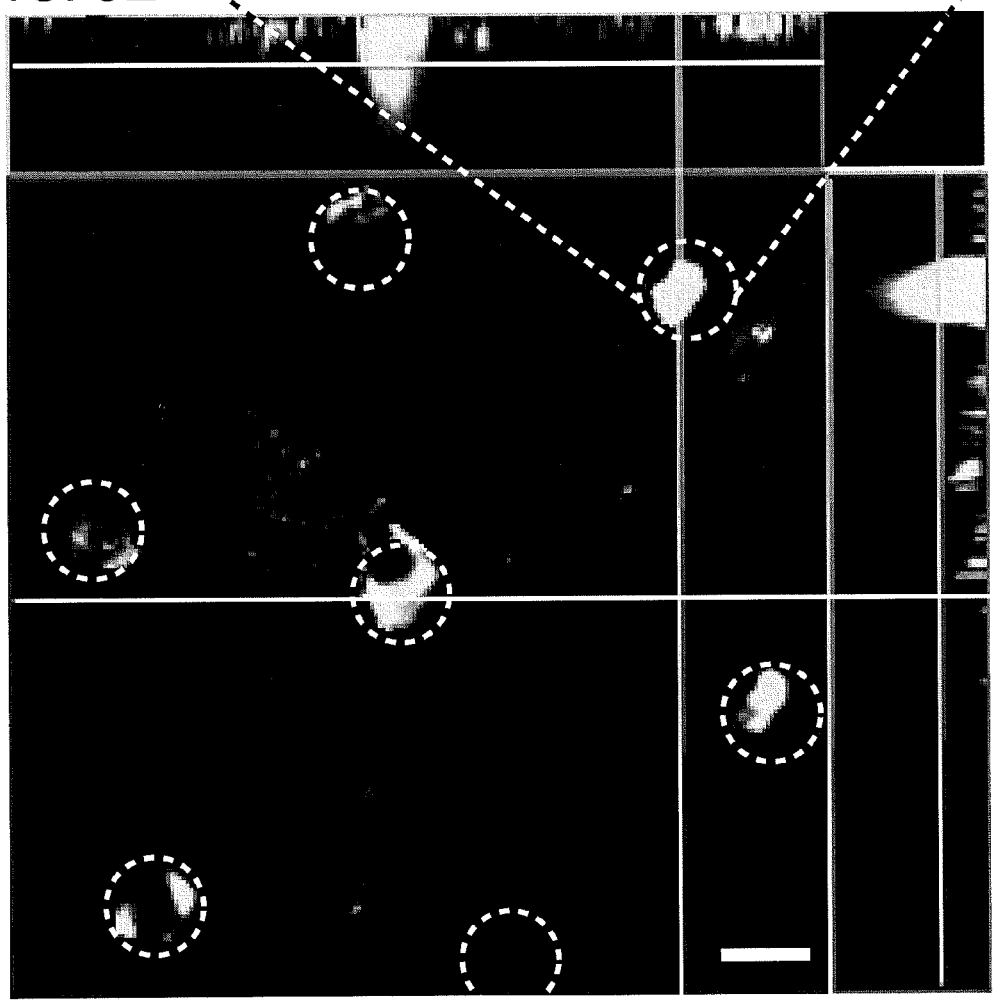
Figure 3F:
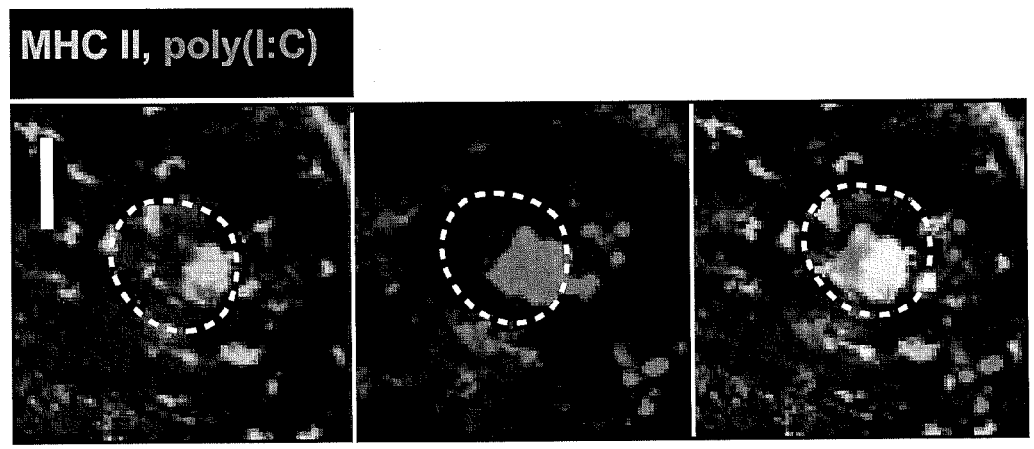
Figure 3G:
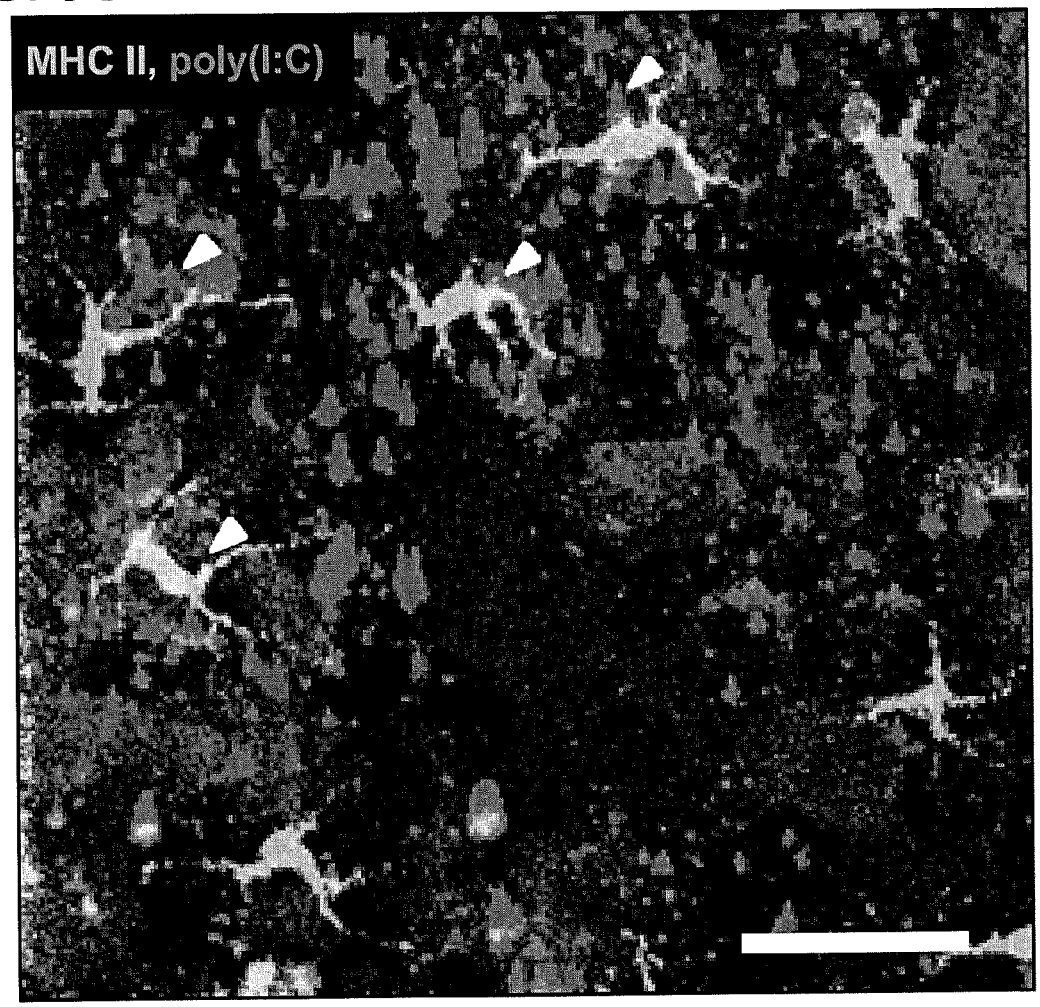

To test whether microneedles coated with "quick release" PEM films would permit rapid PEM film implantation in vivo, we applied dry PNMP-PEM-coated PLLA microneedles to the dorsal ear skin of C57Bl/6-MHC II-GFP mice, transgenic animals expressing green fluorescent protein (GFP) fused to class II major histocompatibility complex (MHC) molecules. The MHC II-GFP fusion protein provides an in situ marker for the viable epidermis, as fluorescent epidermal MHC II$^+$ Langerhans cells (LCs) residing in the tissue are readily detected by confocal microscopy. As expected from prior studies of microneedle arrays fabricated from PLLA, trypan blue staining of skin following microneedle patch application with gentle pressure showed consistent and uniform microneedle penetration (FIG. 3a). Mirroring our in vitro observations, confocal imaging of microneedles after application of the patches to murine skin showed that both uv-bPNMP and Cy5-pLUC fluorescence was rapidly lost from coated microneedles, but only if PNMP films were irradiated before microneedle coating to prime for rapid dissolution of the release layer (FIG. 3b, c). To determine whether PEM films released from microneedles were in fact deposited in the skin, we performed confocal optical sectioning on skin samples following application of PNMP-PEM-coated microneedle arrays. Application of microneedles to skin for 15 min when the release layer was not UV primed resulted in no detectable Cy5-pLUC delivery into the skin (data not shown). By contrast, application of UV-primed microneedles for the same time led to significant transfer of Cy5-pLUC both in the upper epidermis co-localized with GFP+ Langerhans cells (FIG. 3d) and up to 400 µm deep into the skin (FIG. 3e). Similarly, microneedles carrying poly(I:C)-loaded PEM films deposited fluorescently-labeled poly(I:C) into the skin, colocalizing in the same z-plane with MHC II-expressing cell populations (FIG. 3f, g and FIG. 10). In both cases, confocal z-stacks of treated skin indicated the consistent deposition of pLUC and poly(I:C) 300-400 µm below the skin surface at sites of microneedle penetration (FIG. 3e and FIG. 10). Thus, the uv-PNMP release layer promotes rapid implantation of DNA- or RNA-loaded films into the skin.

Figure 4B:
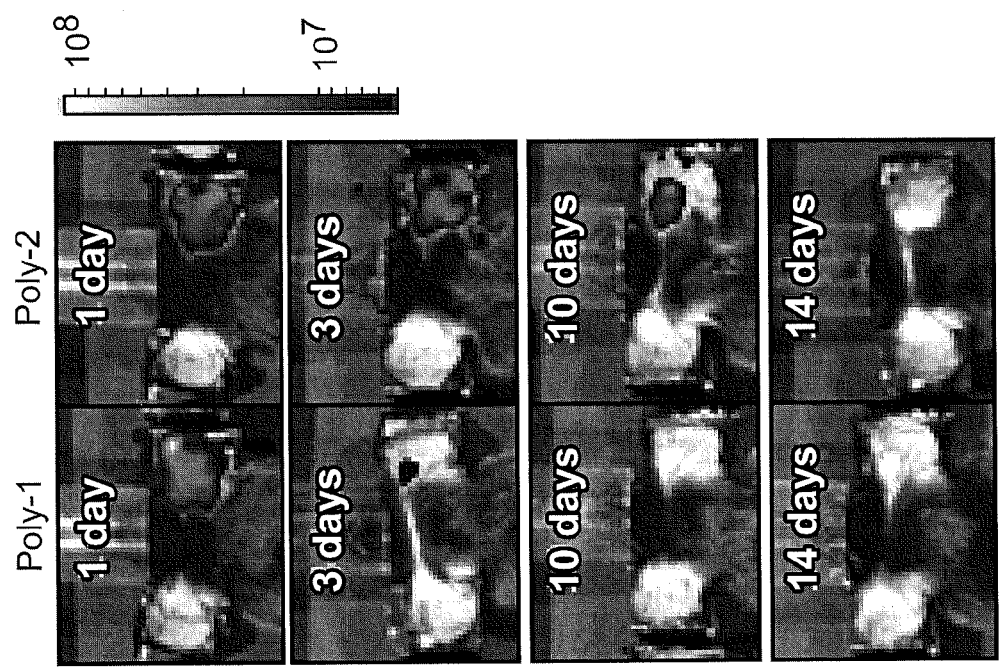
FIG. 4 illustrates that implanted films control and sustain release of pDNA and poly(I:C) in vivo. a, In vitro release of poly(I:C) from $(PS/SPS)_{20}$-$(PBAE/poly(I:C))_{35}$ films on silicon. b, Whole animal fluorescence images of TMR-poly(I:C) retention at application site 1, 3, 10, and 14 days after 15 minute uv-PNMP-$(PS/SPS)_{20}$-$(PBAE/TMR-poly(I:C))_{35}$ coated PLLA microneedle array application, for poly-1 and poly-2. c, Quantification of fluorescence imaging of TMR-poly(I:C) clearance from application site. d, Whole animal bioluminescence images of pLUC expression at application site 1 h, 3, 10, or 20 days after 15 minute uv-PNMP-$(PS/SPS)_{20}$-$(PBAE/pLUC)_{35}$ coated PLLA microneedle array application, for poly-1 and poly-2. e, Quantification of bioluminescence intensity at application site.
Figure 4A:
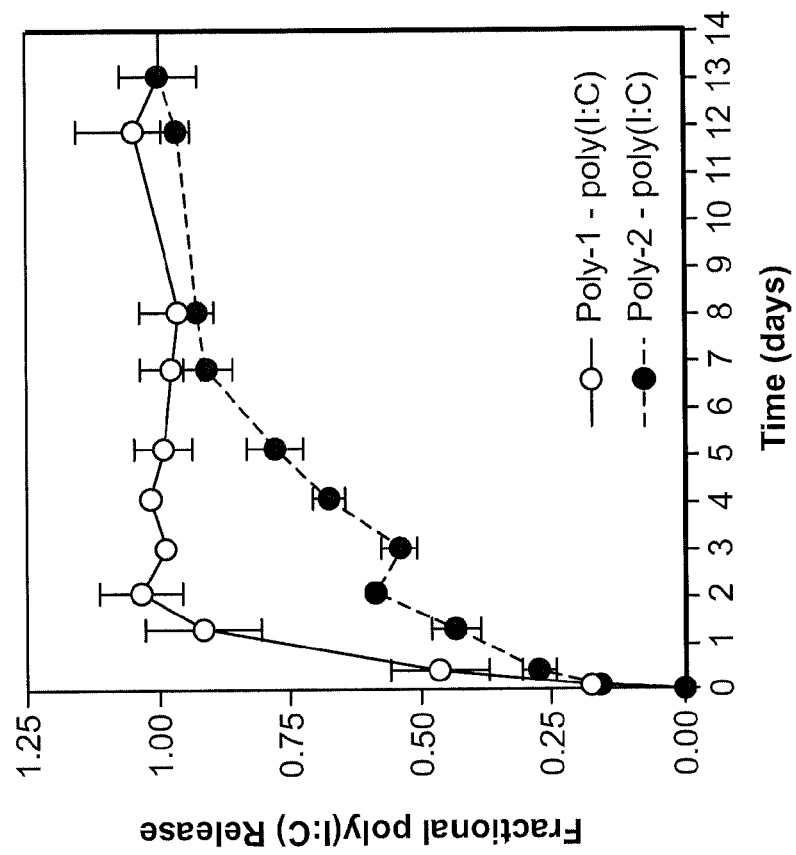

We also tested whether the in vivo kinetics of nucleic acid release into the surrounding tissue could be controlled via the composition of the multi-layers implanted in the skin. Past studies have demonstrated the ability of PEM films to provide controlled release of nucleic acids and promote transfection by released DNA in vitro, and multi-layers composed of pDNA assembled with the PBAEs poly-1 or poly-2 have previously been shown to mediate the release of pDNA with varying kinetics, and to generate polymer-pDNA polyplexes in situ. Consistent with these prior studies, $(PS/SPS)_{20}$-(poly-1/poly(I:C))$_{35}$ and $(PS/SPS)_{20}$-(poly-1/pLUC)$_{35}$ multi-layers constructed on Si substrates and incubated in PBS at 37° C. in vitro exhibited a substantial burst release of ~80% pLUC or poly(I:C) within 24 hr, while analogous films constructed with poly-2 showed a lower burst release of ~35% followed by nearly zero-order release kinetics for 10 days (FIG. 4a and FIG. 11). Dynamic light scattering analysis of eroded films revealed large aggregates (50-300 nm, data not shown) consistent with previous evidence of in situ polyplex formation. To determine whether the composition of PBAE films implanted via microneedle delivery could mediate similar tunable release of nucleic acid therapeutics in vivo, we constructed multi-layer films composed of Cy5-poly(I:C) assembled with either poly-1 or poly-2 on PNMP-coated microneedles as before. Following application of the coated microneedles to the skin of C57Bl/6 mice for 15 min, we monitored the fluorescence signal of Cy5-poly(I:C) implanted in the skin over time using whole animal fluorescence imaging (FIG. 4b). The results show that similar to the in vitro trend, films encapsulating Cy5-poly(I:C) with poly-1 are cleared from the application site within 3 days. Conversely, Cy5-poly(I:C) signal was observed in mice treated with poly-2 film variants for 10 days following application, with clearance following kinetics similar to those seen in vitro (FIG. 4c). Thus, the composition of the PEM films delivered by microneedle tattooing can directly control the release and clearance of their nucleic acid cargos in the skin.

Figure 4E:
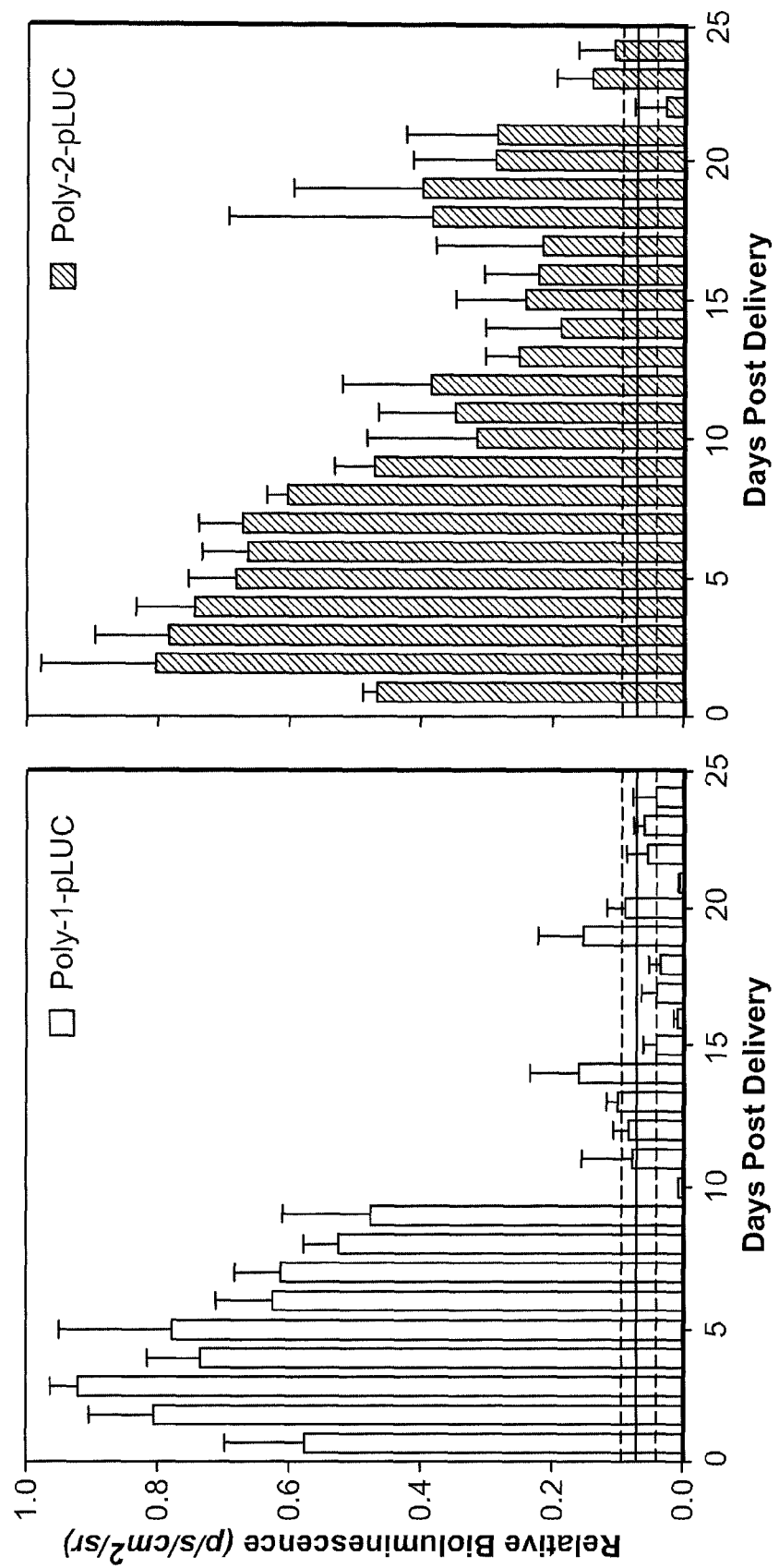

Polymers, poly-1 and poly-2, as exemplary polycation components of these PEM coatings were selected because of not only their biodegradable nature and ability to regulate the rate of release of nucleic acid cargos from films, but also their important role in directly promoting transfection of released pDNA, via the in situ formation of polyplexes during film degradation and plasmid release. To test whether the composition of PBAE/pDNA multi-layers could predetermine the kinetics of the DNA cargo bioactivity in vivo (i.e. transfection), we used whole animal bioluminescence imaging to longitudinally monitor expression of luciferase following pLUC delivery by microneedles. Microneedles were prepared with PNMP-(PBAE/pLUC) coatings, with or without UV priming of the PNMP release layer. Application of control microneedles (where the release layer was not UV primed) to the skin of mice for 15 minutes led to no detectable expression of pLUC (FIG. 12), consistent with the lack of detectable film transfer into skin under this condition. By contrast, the skin of mice treated with microneedles coated with uv-PNMP/(PBAE/pLUC) films showed significant levels of bioluminescence one day after application, demonstrating transfection of cells in situ (FIG. 4d, e). Further, the kinetics of pLUC expression varied greatly depending on the PBAE selected as the complimentary polycation. In the case of skin tattooed with (poly-1/pLUC) multi-layers, luciferase expression peaked sharply after three days and declined to background levels 10 days after treatment, while implantation of slower-degrading (poly-2/pLUC) films showed a slower increase in bioluminescence, peaking and remaining consistent from day 3-7, and then slowly decreasing to background levels by day 22 (FIG. 4e). Together these results demonstrate the potential to control the level and duration of plasmid expression in vivo through selection of constituent polymers with varying half-lives of degradation.

Figure 5A:
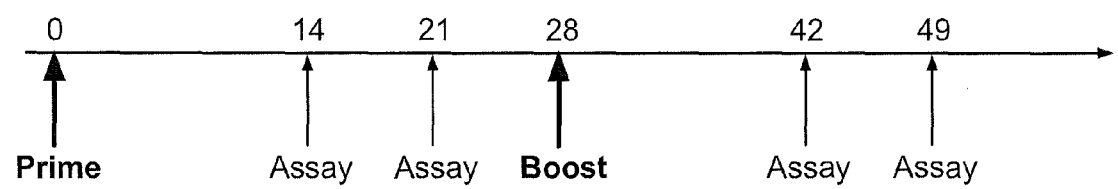
FIG. 5 demonstrates that microneedle-film delivery gives potent cellular and humoral immunity against HIV-Gag. a, C57Bl/6 mice were immunized with 20 µg pGag and 10 µg poly(I:C) on day 0 and 28 intramuscularly (IM±EP) in the quadriceps, intradermally (ID) in the dorsal ear skin, or by 15 minute application of uv-PNMP-$(PS/SPS)_{20}$-$(poly-1/poly(I:C))_{35}$-$(poly-1/pLUC)_{35}$ coated microneedles (MN) at the dorsal ear skin. b, Enzyme-linked-immunosorbent assay analysis of total Gag-specific IgG in sera at d42. c, Frequency of Gag-specific T cells in peripheral blood assessed by flow cytometry analysis of tetramer$^+$ CD8$^+$ T cells. Shown are representative cytometry plots from individual mice at d42 and d, mean tetramer$^+$ values from d21 and d42. e, Analysis of T-cell effector/central memory phenotypes in peripheral blood by CD44/CD62L staining on tetramer+ cells from peripheral blood. Shown are representative cytometry plots from individual mice at d49 and f, mean percentages of tetramer$^+$CD44$^+$CD62L$^+$ among CD8$^+$ T cells at d28 and d49.
Figure 5B:
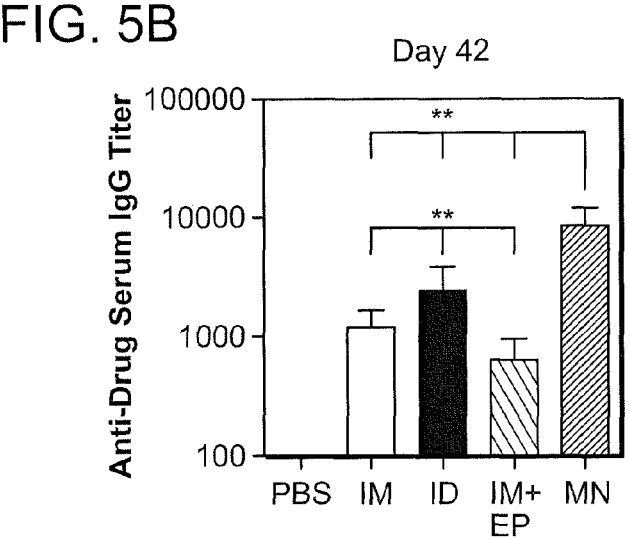
Figure 5C:
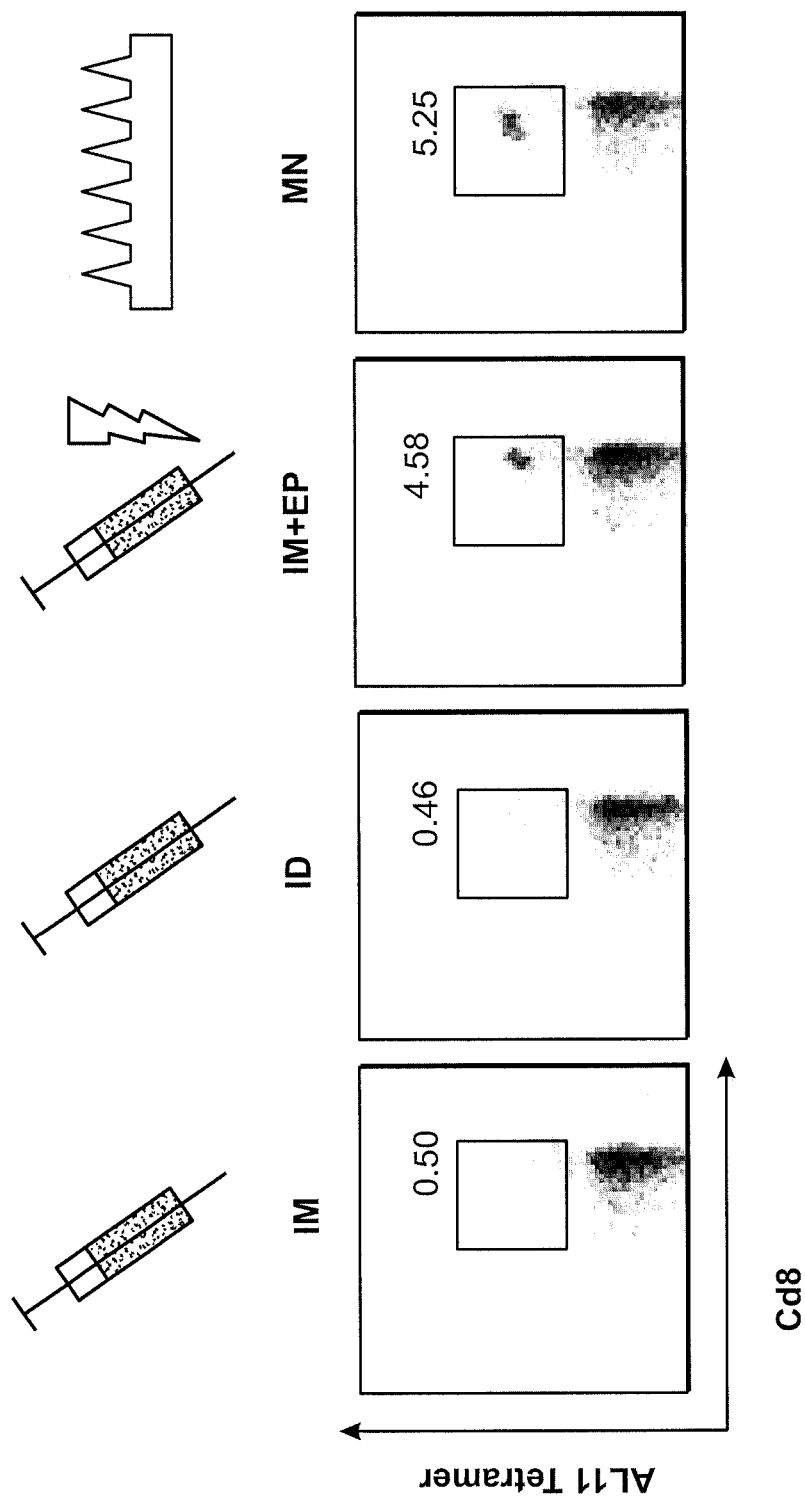
Figure 5D:
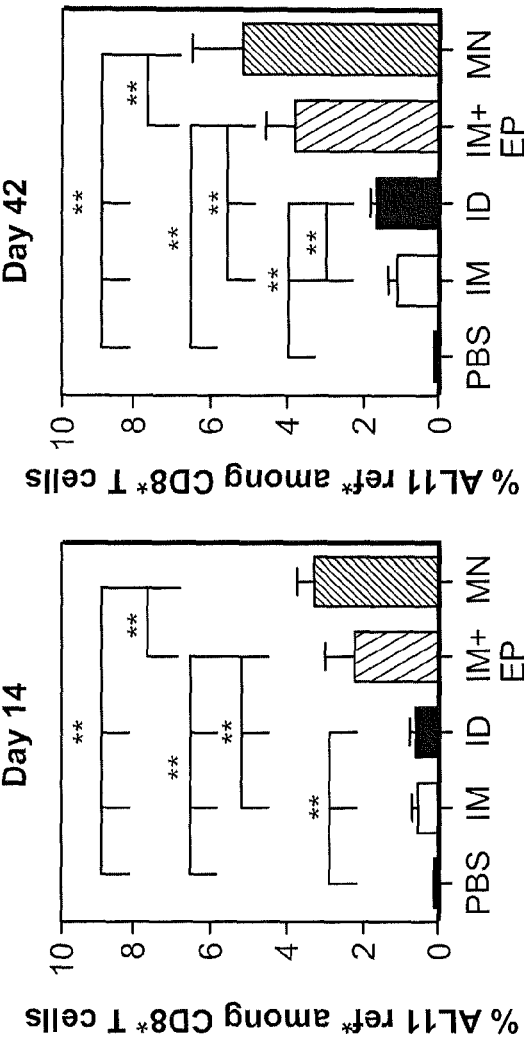
Figure 5E:
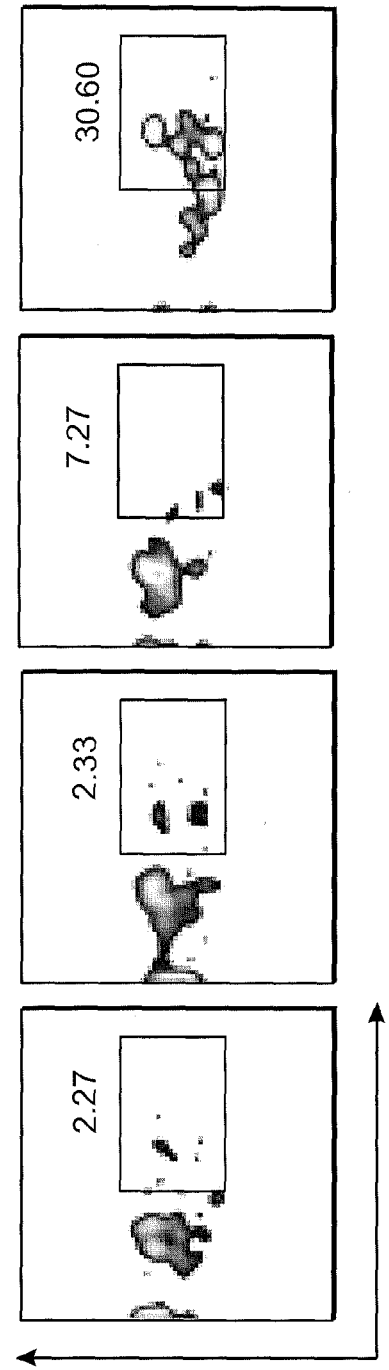
Figure 5F:
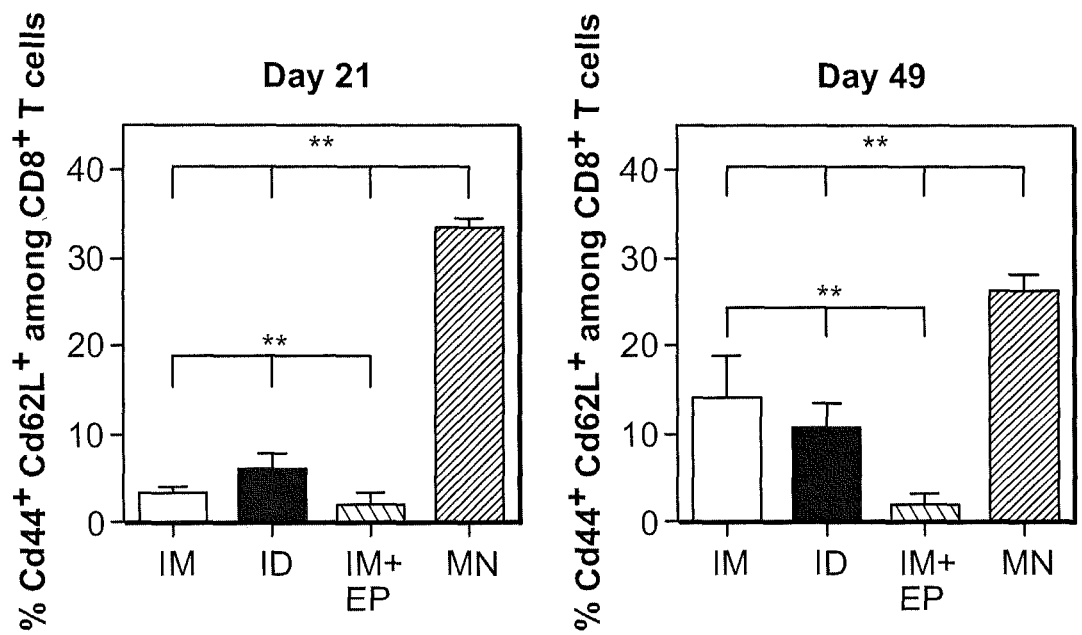
Figure 6A:
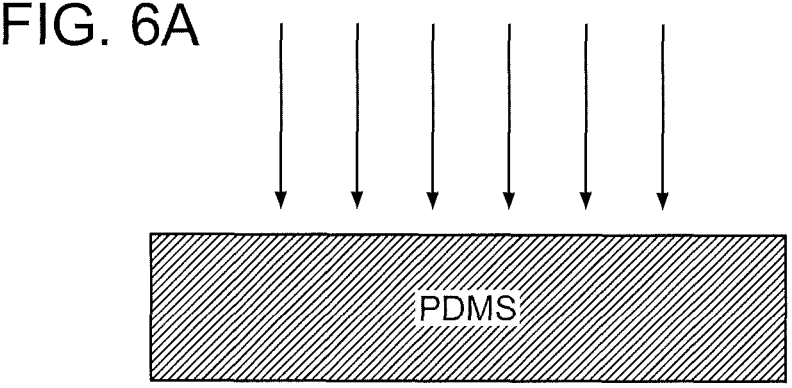
Figure 6B:
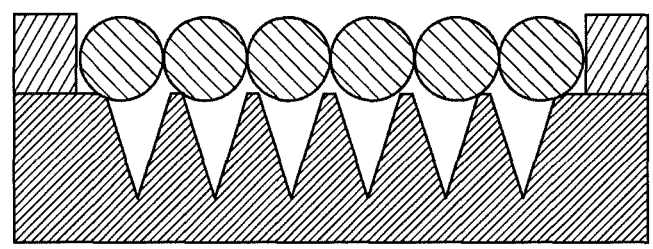
Figure 6C:
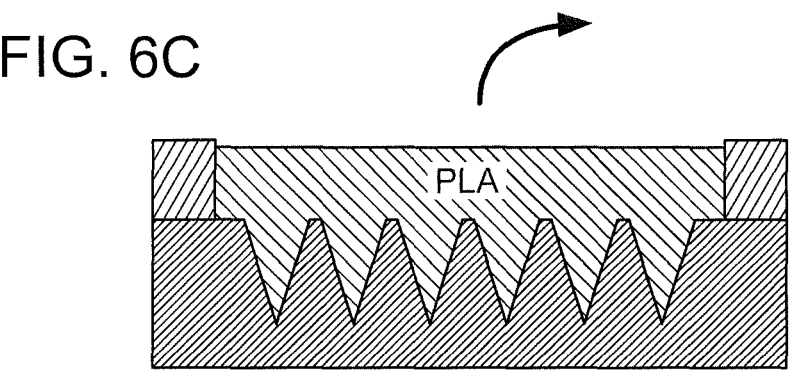
Figure 6D:
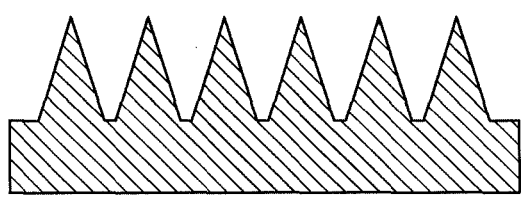
Figure 6E:
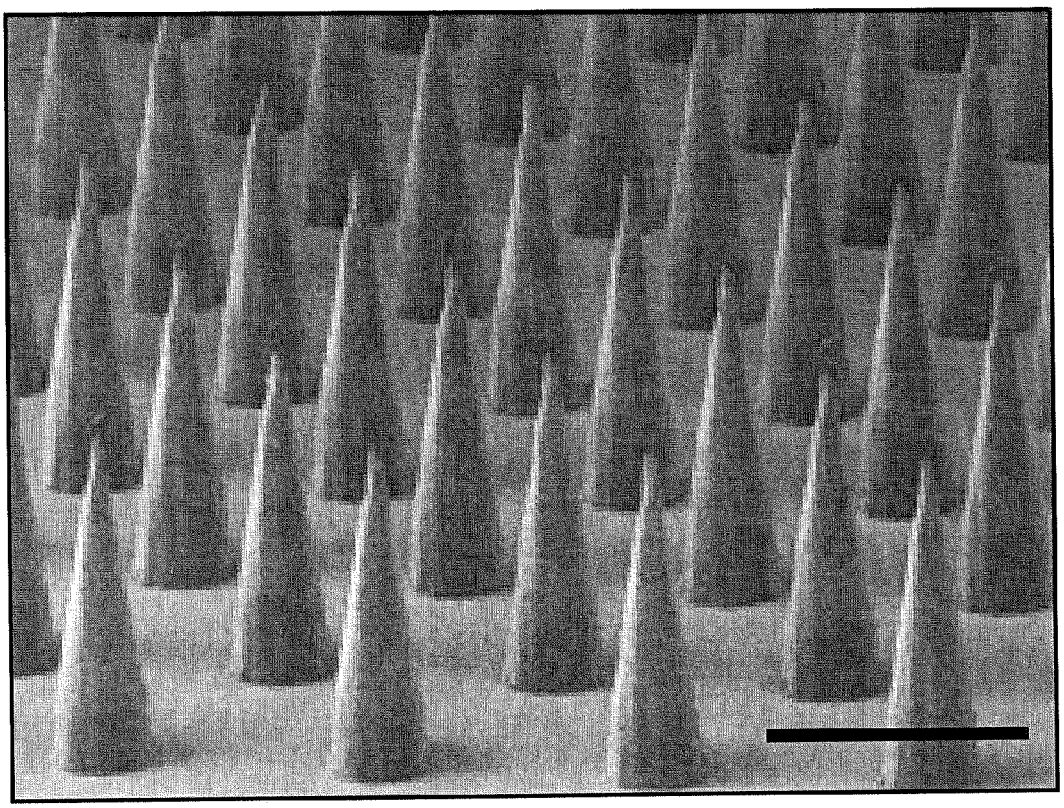
Figure 6F:
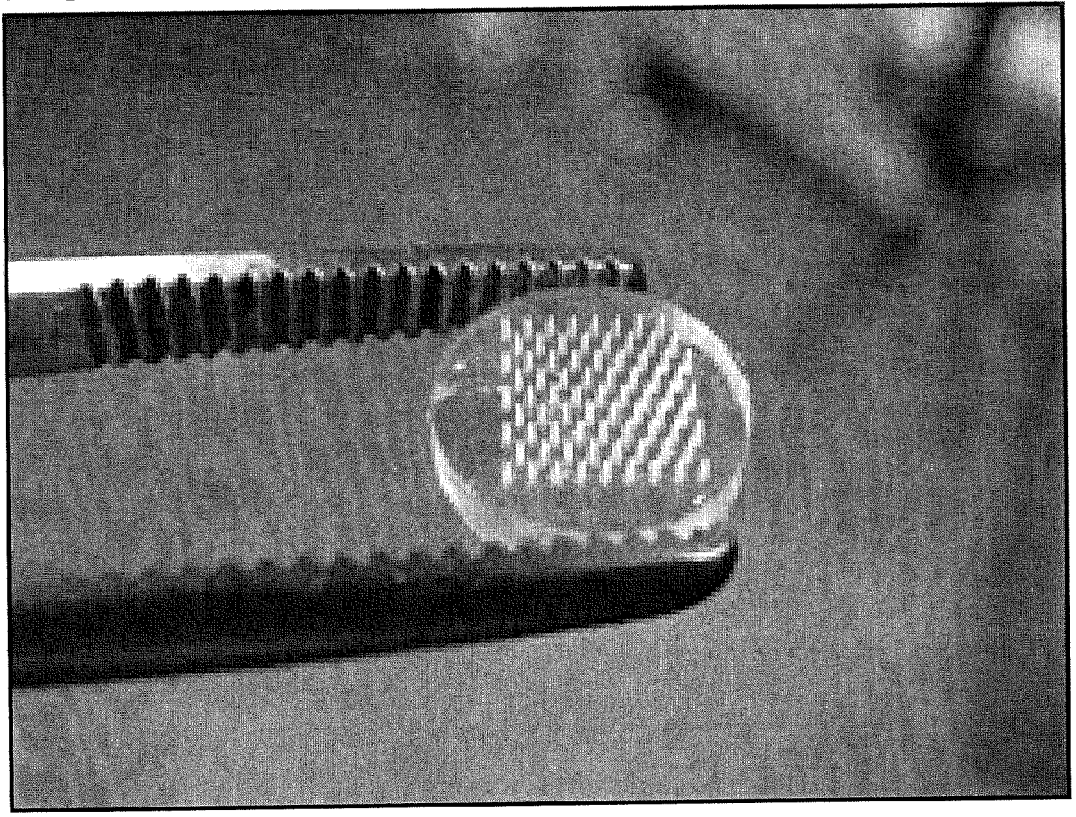
Figure 8B:
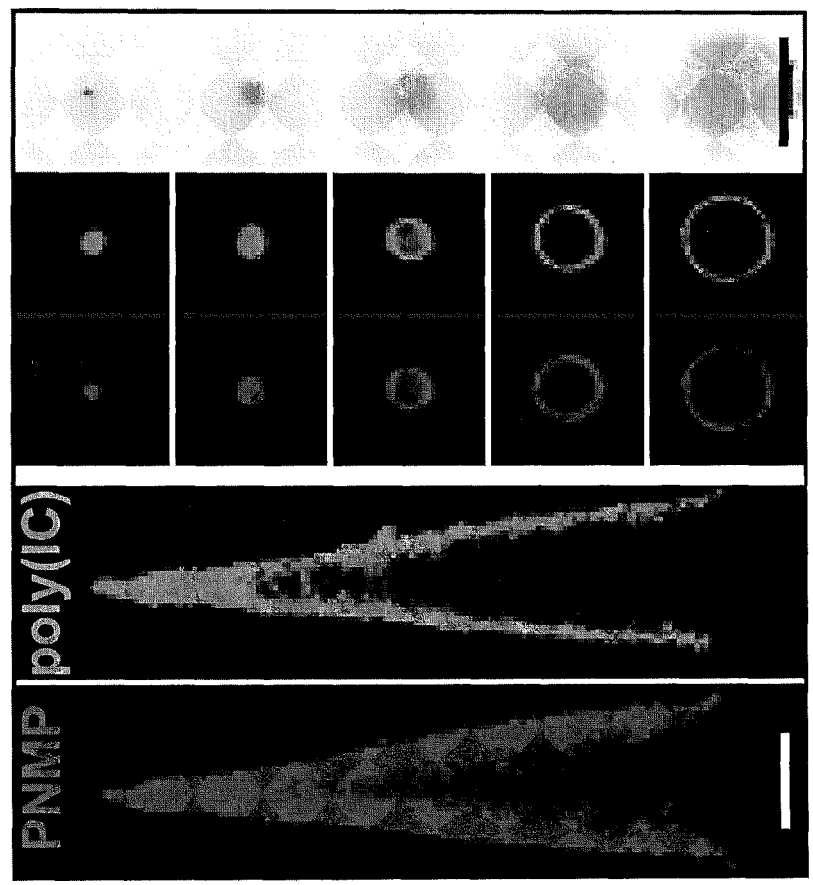
Figure 8A:
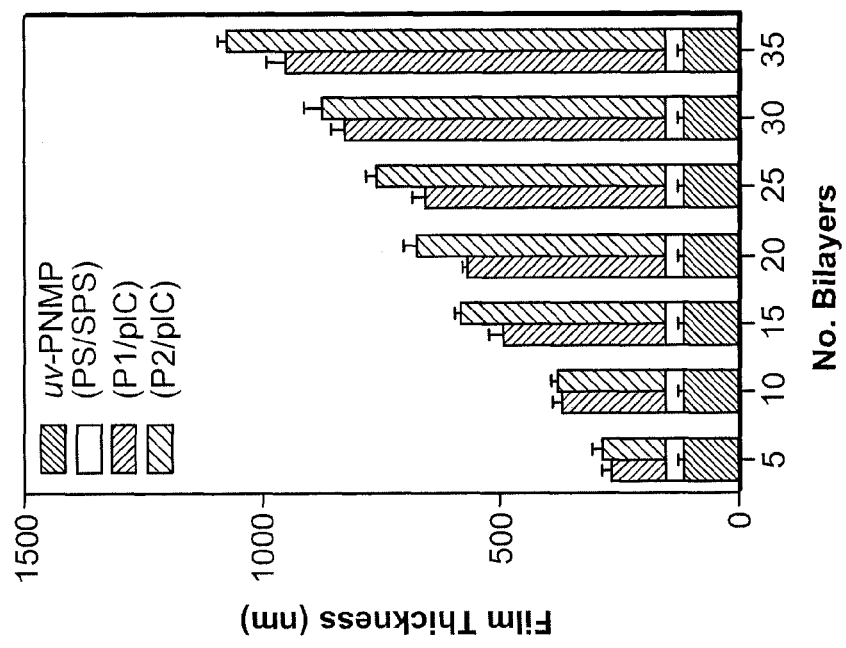
Figure 8D:
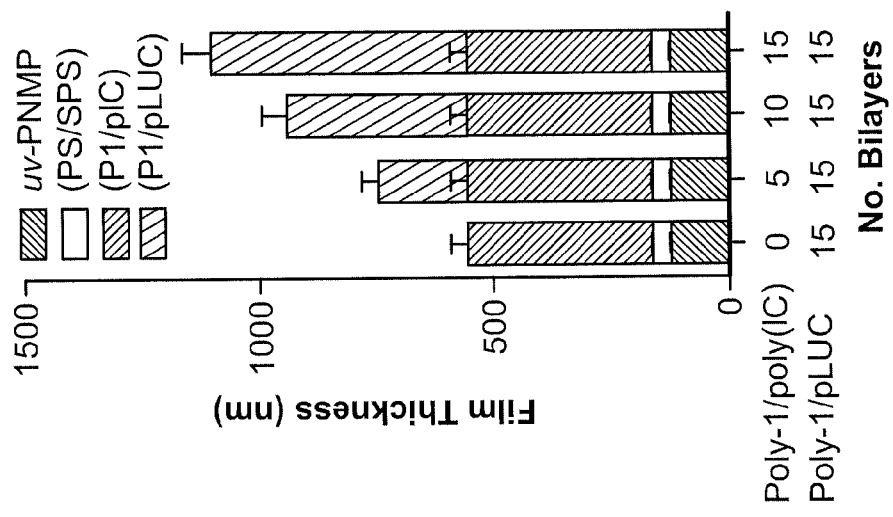
Figure 8C:
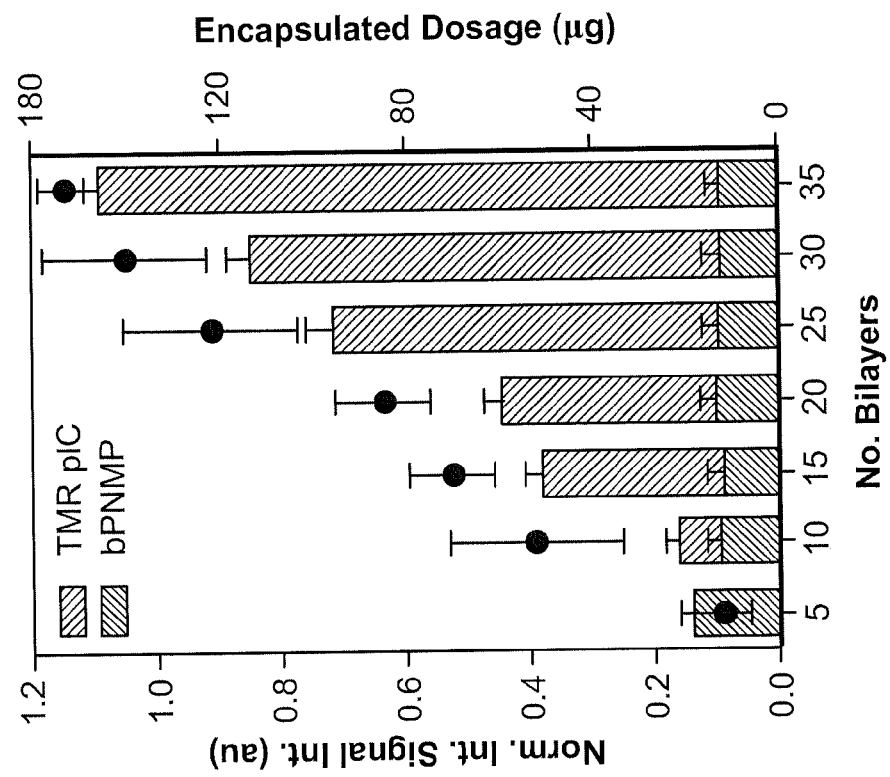

It is contemplated herein that polymer multi-layer tattooing could be utilized for enhancing the efficacy of DNA vaccines, by (1) targeting DNA to skin tissue rich in antigen-presenting cells, (2) promoting transfection of antigen-encoding DNA via in situ polyplex formation/release from multi-layer films, and (3) co-incorporation of nucleic-acid based adjuvant molecules to promote the immune response. To test this idea, microneedles were coated with PEMs of poly-1 co-assembled with poly(I:C) and pGag, a plasmid encoding a model HIV gag antigen, for immunization of animals transcutaneously via microneedle tattooing (FIG. 5a). Multi-layer tattooing was compared to two control immunizations: injection of "naked" pGag plasmid DNA solutions, the most common experimental strategy for DNA immunization in mice and humans, which relies on spontaneous uptake of DNA following injection in tissues; and in vivo electroporation, where DNA is administered in the presence of an electric field via two locally-applied needle electrodes to promote DNA uptake. Naked DNA immunization elicits immune responses in small animal models but has showed low potency in non-human primates and humans; in vivo electroporation is currently one of the most potent alternative strategies for promoting DNA transfection and vaccine responses, though it lacks practicality for mass vaccination. We immunized groups of animals on days 0 and 28 with 20 µg pGag with 10 µg poly(I:C) via multi-layer tattooing with microneedles (MN) applied to the dorsal ear skin. Control mice received equivalent doses of soluble pGag and poly(I:C) intradermally (ID) in the ear skin, or soluble DNA/RNA given intramuscularly with or without in vivo electroporation (IM±EP). Two weeks following the boost, we measured total Gag-specific IgG titers in sera and observed a significant increase in microneedle treated mice over those given IM±EP and ID immunizations (FIG. 5b). Similarly, we compared the frequency of antigen-specific $CD8^+$ T lymphocytes as well as long-lived $CD44^+$ $CD62L^+$ central memory T cells two weeks and three weeks following prime and boost, respectively. As seen in FIG. 5c-d, IM and ID administration produced only weak antigen-specific $CD8^+$ T cell response, while the microneedle treated groups showed robust expansion of Gag-reactive T cells exceeding 5% of the circulating $CD8^+$ population two weeks following boost. This was quantitatively similar to frequencies observed for IM+EP immunized mice. Additionally, microneedle administration effectively generated greater frequencies of CD44+ CD62L+ central memory T cells, a population shown to be important for recall immunity and long-term protection, three weeks following prime and boost (FIG. 5e-f). This was true even relative to mice receiving IM+EP treatment. Thus, DNA vaccination via polymer multi-layer tattooing shows the potential to match the potency of in vivo electroporation, using a skin patch that can be stored in a dry state, is painlessly applied with no extraneous apparatus, and could be self-applied in minutes.

In summary, we have demonstrated here a new approach to therapeutic delivery in skin via polymer thin film "tattooing", using microneedles to rapidly implant biodegradable drug-loaded multi-layers in the skin enabling the kinetics of release and functionality of diverse drug cargos to be manipulated in situ. DNA vaccination was a test-bed application here, due to the relevance of needle-free vaccines for global health and the need for enhanced DNA vaccination strategies. As one with ordinary skill in the art will appreciate that the adaptability of LBL films for incorporation and controlled release of therapeutics ranging from small-molecule drugs to large macromolecules suggests this approach can be applicable to diverse drug delivery applications. Further, the pH-sensitive release layer strategy employed here is a generalizable approach to create selectively-released multi-layer films. The data shown here demonstrated that multi-layer tattooing is useful to enhance the efficacy of DNA vaccines, a platform technology can be applied universally in vaccine development.

Materials

PNMP was synthesized and biotinylated (bPNMP) as previously reported, and analyzed by NMR and GPC. Poly-1 and poly-2 were synthesized, and analyzed by GPC. pLUC and pGag were a gift from Dr. Daniel Barouch, Beth Israel Deaconess Medical Center. Phycoerythrin-conjugated AL-11/H-2K$^b$ peptide-MHC II tetramers were provided by the NIH tetramer core facility.

PLLA Microneedle Fabrication

PDMS molds (Sylgard 184, Dow Corning) were fabricated by laser ablation using a Clark-MXR CPA-2010 micromachining system (VaxDesign Inc.). PLLA pellets (IV 1.9 dL/g, Lakeshore Biomaterials) were melted over the molds under vacuum (−25 in. Hg) at 200° C. for 40 min, and then cooled to −20° C. before separating the cast microneedle arrays. The resulting microneedle arrays were then treated at 140° C. for 4 hr. Microneedles were characterized using a JEOL 6700F FEG-SEM.

PNMP Release Layer Deposition

For film deposition on atomically flat Si substrates, a 3 wt % PNMP solution in 1,4-dioxane was deposited by spin coating using a Specialty Coating Systems P6700, and then dried under vacuum for 12 hr. For deposition on PLLA microneedles, a 0.25 wt % bPNMP solution was deposited using a modified air-brush as previously described (0.2 mL/s, 15 cm range, 10 s), then dried under vacuum for 12 hr. bPNMP release-layers were labeled using SAv488 (Sigma-Aldrich) at 10 µg/mL in 1×PBS, pH 6.0. Film deposition was characterized using a Veeco Dektak surface profilometer and a JEOL 6700F FEG-SEM.

Polymer Multi-Layer Film Preparation

All LbL films were assembled using a Carl Ziess HMS DS50 slide stainer. Films were constructed on Si wafers and PLLA microneedle arrays following deposition of bPNMP release layers. Prior to multi-layer assembly, the solubility of the PNMP release layer was photoswitched via UV irradiation of coated Si or microneedle substrates (254 nm, 2.25 mW/cm$^2$, UVP) for 15 min. To build (PS/SPS) baselayers, substrates were alternatingly dipped into PS (2 mg/mL, 1×PBS, Sigma-Aldrich) and SPS (5 mM, 1×PBS, Sigma-Aldrich) solutions for 10 min, separated by two sequential 1 min rinses in PBS. (PBAE/pLUC) and (PBAE/poly(I:C)) multi-layers were deposited similarly, alternating 5 min dips in poly-1/2 (2 mg/mL, 1×PBS) and either pLUC, pGag (1 mg/mL, 1×PBS) or poly(I:C) (1 mg/mL, 1×PBS, Invivogen) solutions separated by two sequential 30 sec rinsing steps in 1×PBS. Fluorescent pLUC and poly(I:C) were prepared using Cy5 and tetramethyl-rhodamine (TMR) Label-IT reagent (Mirus Bio Corporation). All solutions were adjusted to pH 5.0 and filtered (0.2 µm, except pLUC, pGag and poly(I:C)) prior to dipping. Films were characterized using a Veeco Dektak surface profilometer and a Zeiss LSM 510. Data analysis was performed using Image J. Film loading was determined using a SpectraMax 250 spectrophotometer following elution of films in 1×PBS, pH 7.4, 2 M NaCl for 24 hours.

In Vitro/In Vivo Delamination/Delivery

For in vitro delamination assays, coated Si wafers were incubated in PBS, pH 7.4 and time-lapse microscopy was performed using a Leica DMXR instrument. For in vitro release (PS/SPS)$_{20}$-(PBAE/pLUC)$_{35}$ or (PS/SPS)$_{20}$-(PBAE/poly(I:C))$_{35}$ films on silicon were incubated in PBS at 37° C. and aliquots were assayed for released pLUC or poly(I:C) using picogreen or ribogreen detection kits (Invitrogen) For in vitro delivery, coated microneedle arrays were incubated in PBS, pH 7.4, dried, and imaged by confocal microscopy. In vivo delivery experiments were performed on anesthetized C57BL/6 mice (Jackson Laboratories) and MHC II-GFP transgenic mice (a gift from Prof. Hidde Ploegh). Ears were rinsed briefly with PBS on the dorsal side and dried before application of microneedle arrays by gentle pressure. Following application, microneedles were dried and imaged by confocal. Treated mice were sacrificed and excised ears were stained with trypan blue before imaging for needle penetration. Ears collected from mice treated with Cy5-pLUC- or TMR-poly(I:C)-coated microneedles (+UV-treatment) were mounted on glass slides and imaged by confocal. Clearance of fluorescent poly(I:C) and transfection in mice treated with pLUC-coated arrays (+UV-treatment) was measured using an IVIS Spectrum 200 (Caliper Lifesciences) to detect fluorescence and bioluminescence respectively. Bioluminescence was measured following IP injection of luciferin and data analysis was performed using the Living Image Software package.

Vaccinations

All animal studies were approved by the MIT IUCAC and animals were cared for in the USDA-inspected MIT Animal Facility under federal, state, local, and NIH guidelines for animal care. Groups of 4 C57Bl/6 mice were immunized with 20 µg pGag and 10 µg poly(I:C) by intramuscular injection (15 µl in the quadriceps) with or without in vivo electroporation (performed according to the manufacturer's instructions, Harvard Apparatus ECM830, 2×60 ms pulses, 200 V/cm), intradermal injection (15 µl in the dorsal caudal ear skin) or by microneedle array (15 min application of (PS/SPS)$_{20}$-(poly-1/poly(I:C))$_{35}$-(poly-1/pGag)$_{35}$ on UV-treated PNMP coated PLLA arrays). Frequencies of Gag-specific CD8+ T-cells and their phenotypes elicited by immunization were determined by flow cytometry analysis of peripheral blood mononuclear cells at selected time points following staining with DAPI (to discriminate live/dead cells), anti-CD8α, anti-CD44, anti-CD62L, and phycoerythrin-conjugated AL-11/H-2K$^b$ peptide-MHC tetramers. Anti- Gag IgG titers, defined as the dilution of sera at which 450 nm OD reading was 0.25, were determined by ELISA analysis of sera from immunized mice. Animals were cared for following NIH, state, and local guidelines.

Statistical Analysis

Statistical analysis was carried out with Graphpad Prism (La Jolla, Calif.). Data was analyzed using two-way analysis of variance or t-test. p-values less than 0.05 were statistically significant. All values are reported as mean±s.e.m.

OTHER EMBODIMENTS AND EQUIVALENTS

While the present disclosures have been described in conjunction with various embodiments and examples, it is not intended that they be limited to such embodiments or examples. On the contrary, the disclosures encompass various alternatives, modifications, and equivalents, as will be appreciated by those of skill in the art. Accordingly, the descriptions, methods and diagrams of should not be read as limited to the described order of elements unless stated to that effect.

Although this disclosure has described and illustrated certain embodiments, it is to be understood that the disclosure is not restricted to those particular embodiments. Rather, the disclosure includes all embodiments that are functional and/or equivalents of the specific embodiments and features that have been described and illustrated.

We claim:

1. A structure, comprising:
   a substrate, comprising a microneedle array;
   a release layer disposed on the substrate; and
   a controlled delivery layer disposed on the release layer, wherein the controlled delivery layer comprises one or more layer-by-layer (LBL) films and a nucleic acid.

2. The structure of claim 1, wherein the release layer comprises a polymer, the polymer being a photocleavable polymer, convertible into a photocleaved polymer.

3. The structure of claim 2, wherein the photocleaved polymer is pH sensitive, so that it is stable in a predetermined pH range but unstable at or near physiological pH.

4. The structure of claim 2, wherein the photocleaved polymer is substantially less soluble at pH of 6.5 or below than at a pH of 6.5 or greater.

5. The structure of claim 2, wherein the photocleavable polymer is a terpolymer of a hydrophobic monomer, a hydrophilic monomer, and an additional monomer having a side group represented by the following structural formula:

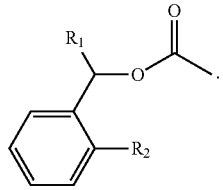

6. The structure of claim 5, wherein the hydrophobic monomer is selected from methyl methacrylate, ethyl methacrylate, n-butyl methacrylate, n-decyl methacrylate, 2-ethylhexyl methacrylate, N-(n-octadecyl)acrylamide, n-tert-octylacrylamide, stearyl acrylate, stearyl methacrylate, and vinyl stearate.

7. The structure of claim 5, wherein the hydrophilic monomer is selected from hydroxyethylmethacrylate, hydroxyethyl acrylate, 4-hydroxybutyl methacrylate, N-(2-hydroxypropyl)methacrylamide, n-methylmethacrylamide, acrylamide, poly(ethylene glycol) monomethyl ether methacrylates, poly(ethylene glycol) methacrylate, poly(ethylene glycol) methacrylates, and n-vinyl-2-pyrrolidone.

8. The structure of claim 5, wherein the additional monomer is photocleavable to a carboxyl group.

9. The structure of claim 2, wherein the photocleavable polymer is a terpolymer of methyl methacrylate, poly(ethylene glycol) methacrylate, and o-nitrobenzyl methacrylate.

10. The structure of claim 1, wherein the LBL films comprises a first plurality of a first unit.

11. The structure of claim 10, wherein the LBL films further comprise a second plurality of a second unit.

12. The structure of claim 1, wherein at least a portion of the LBL films comprises alternating polycationic and polyanionic layers, and degradation of the LBL films is characterized by hydrolytic degradation of at least a portion of a one of the polycationic layers, one of the polyanionic layers, or both.

13. The structure of claim 1, wherein at least a portion of the LBL films comprises a degradable polyelectrolyte.

14. The structure of claim 13, wherein the degradable polyelectrolyte comprises a polymer selected from polyester, polyanhydride, polyorthoester, polyphosphazene, and polyphosphoester, or any combination thereof.

15. The structure of claim 14, wherein the degradable polyelectrolyte comprises the polyester selected from a group consisting of poly(β-amino ester)s, poly(L-lactide-co-L-lysine), poly(serine ester), poly(4-hydroxy-L-proline ester), and poly[.alpha.-(4-aminobutyl)-L-glycolic acid], or any combination thereof.

16. The structure of claim 15, wherein the polyester is the poly((3-amino ester) selected from the group consisting of

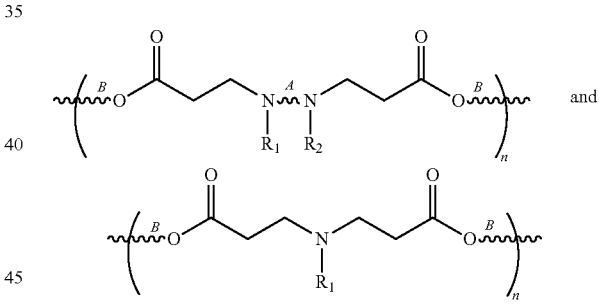

wherein:
linker A and linker B are each independently selected from the group consisting of carbon chains of 1 to 30 carbon atoms, heteroatom-containing carbon chains of 1 to 30 atoms, and carbon chains and heteroatom-containing carbon chains with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups;

$R_1$ and $R_2$ are each independently selected from the group consisting of hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups; and n is an integer greater than or equal to 5.

17. The structure of claim 15, wherein the polyester is the poly(β-amino ester) selected from the group consisting of cyclic aromatic, heterocyclic, and aromatic heterocyclic groups, each of which may be substituted with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups; and n is an integer greater than or equal to 5.

18. The structure of claim 15, wherein the poly(β-amino ester) is selected from the group consisting of

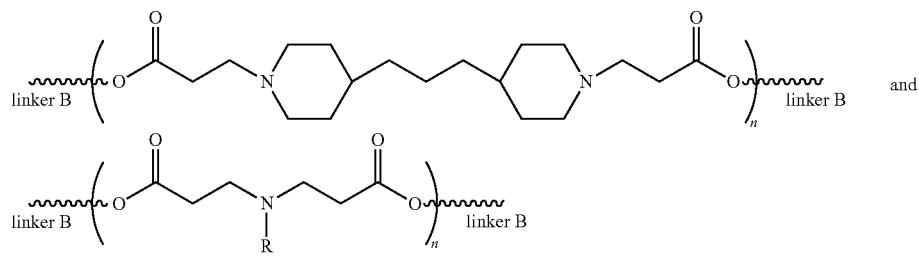

wherein:

linker B is independently selected from the group consisting of carbon chains of 1 to 30 carbon atoms, heteroatom-containing carbon chains of 1 to 30 atoms, and carbon chains and heteroatom-containing carbon chains with at least one substituent selected from the

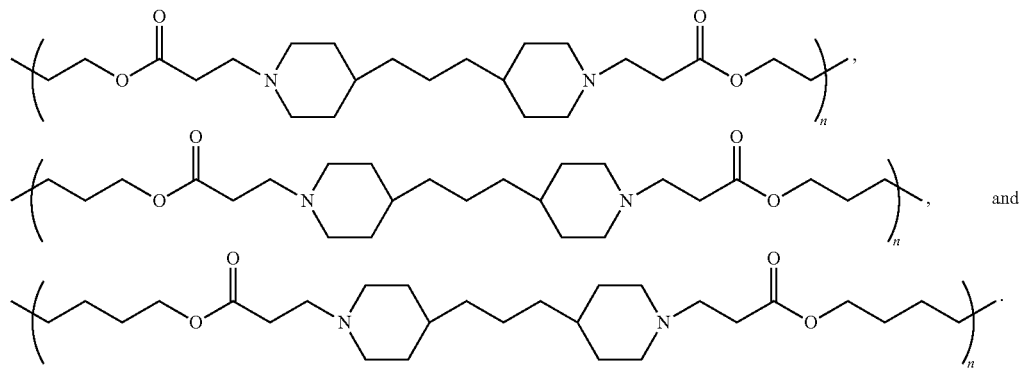

group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups;

R is selected from the group consisting of hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, 19. The structure of claim 1 wherein the nucleic acid comprises a therapeutic gene.

20. The structure of claim 1, wherein the nucleic acid comprises a plasmid DNA.

21. The structure of claim 1 wherein the nucleic acid comprises a plasmid DNA, and wherein the controlled delivery layer further includes a polymeric transfection agent and an adjuvant.

22. A method of making a structure, comprising
 a substrate, comprising a microneedle array;
 a release layer disposed on the substrate; and
 a controlled delivery layer disposed on the release layer,
  wherein the controlled delivery layer comprises one or more layer-by-layer (LBL) films and a nucleic acid, the method comprising a steps of:

coating the substrate with the release layer; and coating the release layer with the controlled delivery layer.

23. The method of claim 22, further comprising altering the property of the release layer to allow the release of the controlled delivery layer under certain conditions.

24. The method of claim 23, wherein the release layer is comprises a photocleavable polymer and the step of altering the property of the release layer comprises exposing the release layer to UV to obtain a photocleaved polymer.

25. The method of claim 24, wherein the photocleaved polymer is pH sensitive, so that it is stable in a predetermined pH range but unstable at or near physiological pH.

26. The method of claim 23, wherein the step of altering the property of the release layer is performed before the step of coating the release layer with the controlled delivery layer.

27. The method of claim 22, further comprising incorporating a nucleic acid into the controlled delivery layer.

28. A method of delivering a nucleic acid to a subject in need thereof, the method comprising:

providing a structure, comprising:

a substrate, comprising a microneedle array;

a release layer disposed on the substrate; and a controlled delivery layer disposed on the release layer, wherein the controlled delivery layer comprises one or more layer-by-layer (LBL) films and a nucleic acid; and contacting an application site on the subject with the structure so that the release layer releases the controlled delivery layer from the substrate into the application site.

29. The method of claim 28, further including removing the substrate from the application site.

* * * * *